US007714159B2

(12) United States Patent
Pickersgill et al.

(10) Patent No.: US 7,714,159 B2
(45) Date of Patent: May 11, 2010

(54) SYNTHESIS OF BORONIC ESTER AND ACID COMPOUNDS

(75) Inventors: I. Fraser Pickersgill, Newton, PA (US); John E. Bishop, Groton, MA (US); Christoph Koellner, Bubendorf (CH); Jean-Marc Gomez, Bubendorf (CH); Achim Geiser, Hunzenschwil (CH); Robert Hett, Hunzenschwil (CH)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1090 days.

(21) Appl. No.: 11/088,667

(22) Filed: Mar. 24, 2005

(65) Prior Publication Data

US 2005/0240047 A1 Oct. 27, 2005

Related U.S. Application Data

(60) Provisional application No. 60/557,535, filed on Mar. 30, 2004.

(51) Int. Cl.
*C07F 558/288* (2006.01)
(52) U.S. Cl. .................................. 558/288
(58) Field of Classification Search .................. 558/288
See application file for complete search history.

(56) References Cited

U.S. PATENT DOCUMENTS

| | | | |
|---|---|---|---|
| 4,499,082 | A | 2/1985 | Shenvi et al. |
| 4,525,309 | A | 6/1985 | Matteson et al. |
| 4,537,773 | A | 8/1985 | Shenvi |
| 4,701,545 | A | 10/1987 | Matteson et al. |
| 5,106,948 | A | 4/1992 | Kinder et al. |
| 5,169,841 | A | 12/1992 | Kleeman et al. |
| 5,187,157 | A | 2/1993 | Kettner et al. |
| 5,242,904 | A | 9/1993 | Kettner et al. |
| 5,250,720 | A | 10/1993 | Kettner et al. |
| 5,780,454 | A | 7/1998 | Adams et al. |
| 6,066,730 | A | 5/2000 | Adams et al. |
| 6,699,835 | B2 | 3/2004 | Plamondon et al. |

OTHER PUBLICATIONS

Carmes et al., Journal of Organic Chemistry, 2000, 65, pp. 5403-5408.*
Matteson et al., Journal of the American Chemical society, 1983, 105, pp. 2077-2078.*
Ether, Wikipedia, the free encyclopedia.*
Pergament, Inna, et al., "Arbuzov reaction of 1-iodoboronates as a means of preparing C1-bridged phosphonoboronates," *Tetrahedron Letters*, vol. 40 (1999) pp. 3895-3898.
Dou, Q. Ping, et al., "Bortezomib Millennium Pharmaceuticals," *IDrugs*, vol. 5, No. 8 (2002) pp. 828-834.

Dunsdon, Rachel M., et al., "Solid phase synthesis of aminoboronic acids: potent inhibitors of the hepatitis C virus NS3 proteinase," *Bioorganic & Medicinal Chemistry Letters*, vol. 10, No. 14 (2000) pp. 1577-1579.
Von Matt, Anette, et al., "Selective boron-containing thrombin inhibitors—x-ray analysis reveals surprising binding mode," *Biorganic & Medicinal Chemistry*, vol. 8, No. 9, (2000) pp. 2291-2303.
Search Report and Written Opinion of the International Searching Authority in International Application No. PCT/US2005/009774, WO2005/097809, which corresponds to U.S. Appl. No. 11/088,667.
Brown, Herbert C., et al., "Organoboranes. 30. Convenient Procedures for the Synthesis of Alkyl- and Alkenylboronic Acids and Esters," *Organometallics*, vol. 2, No. 10, pp. 1311-1316 (1983).
Matteson, Donald S., et al., "Directed Chiral Synthesis with Pinanediol Boronic Esters," *Journal of American Chemical Society*, vol. 102, pp. 7590-7591 (1980).
Matteson, Donald S., et al., "α-Chloro Boronic Esters from Homologation of Boronic Esters," *Journal of American Chemical Society*, vol. 102, pp. 7588-7590 (1980).
Matteson, Donald S., et al., "R-1-Acetamido-2-Phenylethaneboronic Acid, A Specific Transition-State Analogue for Chymotrypsin," *Journal of American Chemical Society*, vol. 103, pp. 5241-5242 (1981).
Matteson, Donald S., et al., "Epimerization of α-Chloro Boronic Esters by Lithium and Zinc Chlorides," *Organometallics*, vol. 2, No. 9, pp. 1083-1088 (1983).
Kettner, Charles A., et al., "Inhibition of the Serine Proteases Leukocyte Elastase, Pancreatic Elastase, Cathepsin G, and Chymotrypsin by Peptide Boronic Acids," *The Journal of Biological Chemistry*, vol. 259, No. 24, pp. 15106-15114 (Dec. 25, 1984).
Matteson, Donald S., et al., "(R)-1-acetamido-2-phenylethaneboronic acid. A specific transition-state analogue for chymotrypsin." *Journal of American Chemical Society.* vol. 103 (1981) pp. 5241-5242.
Matteson, Donald S., et al., "Superoxide-Ion oxidation of hydrophenazines, reduced flavins, hydroxylamine, and related substrates via hydrogen-atom transfer." *Journal of the American Chemical Society*, vol. 102 (1980) pp. 7591-7593.
Matteson, Donald S., et al., "α-chloro boronic esters from homologation of boronic esters," *Journal of the American Chemical Society*, vol. 102 (1980) pp. 7588-7590.
Kolomeitsev, Alexander A., et al., "Perfluoroalkyl borates and boronic esters: new promising partners for Suzuki and Petasis reactions," *Tetrahedron Letters*, vol. 44, pp. 8273-8277 (2003).
Priestley, E. Scott, et al., "P1 Phenethyl Peptide Boronic Acid Inhibitors of HCV NS3 Protease," *Bioorganic & Medicinal Chemistry Letters*, vol. 12, pp. 3199-3202 (2002).

* cited by examiner

*Primary Examiner*—Rei-tsang Shiao

(57) ABSTRACT

The invention relates to the synthesis of boronic ester and acid compounds. More particularly, the invention provides improved synthetic processes for the large-scale production of boronic ester and acid compounds, including the peptide boronic acid proteasome inhibitor bortezomib.

30 Claims, No Drawings

SYNTHESIS OF BORONIC ESTER AND ACID COMPOUNDS

RELATED APPLICATIONS

This application is a nonprovisional of provisional patent application No. 60/557,535, filed on Mar. 30, 2004, the entire contents of which are hereby incorporated by reference.

BACKGROUND OF THE INVENTION

1. Field of the Invention

This invention relates to the synthesis of boronic ester and acid compounds. More particularly, the invention relates to large-scale synthetic processes for the preparation of boronic ester and acid compounds by Lewis acid promoted rearrangement of boron "ate" complexes.

2. Background of the Invention

Boronic acid and ester compounds display a variety of pharmaceutically useful biological activities. Shenvi et al., U.S. Pat. No. 4,499,082 (1985), discloses that peptide boronic acids are inhibitors of certain proteolytic enzymes. Kettner and Shenvi, U.S. Pat. No. 5,187,157 (1993), U.S. Pat. No. 5,242,904 (1993), and U.S. Pat. No. 5,250,720 (1993), describe a class of peptide boronic acids that inhibit trypsin-like proteases. Kleeman et al., U.S. Pat. No. 5,169,841 (1992), discloses N-terminally modified peptide boronic acids that inhibit the action of renin. Kinder et al., U.S. Pat. No. 5,106,948 (1992), discloses that certain tripeptide boronic acid compounds inhibit the growth of cancer cells.

More recently, boronic acid and ester compounds have displayed particular promise as inhibitors of the proteasome, a multicatalytic protease responsible for the majority of intracellular protein turnover. Ciechanover, *Cell*, 79: 13-21 (1994), discloses that the proteasome is the proteolytic component of the ubiquitin-proteasome pathway, in which proteins are targeted for degradation by conjugation to multiple molecules of ubiquitin. Ciechanover also discloses that the ubiquitin-proteasome pathway plays a key role in a variety of important physiological processes.

Adams et al., U.S. Pat. No. 5,780,454 (1998), U.S. Pat. No. 6,066,730 (2000), U.S. Pat. No. 6,083,903 (2000), U.S. Pat. No. 6,297,217 (2001), U.S. Pat. No. 6,548,668, and U.S. Pat. No. 6,617,317 (2003), hereby incorporated by reference in their entirety, describe peptide boronic ester and acid compounds useful as proteasome inhibitors. The references also describe the use of boronic ester and acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, to inhibit antigen presentation in a cell, to inhibit NF-κB dependent cell adhesion, and to inhibit HIV replication.

Albanell and Adams, *Drugs of the Future* 27: 1079-1092 (2002), discloses that one such peptide boronic acid proteasome inhibitor, bortezomib (N-2-pyrazinecarbonyl-L-phenylalanine-L-leucineboronic acid), shows significant antitumor activity in human tumor xenograft models and is undergoing clinical evaluation. Richardson et al., *New Engl. J. Med.*, 348:2609 (2003), reports the results of a Phase 2 study of bortezomib, showing its effectiveness in treating relapsed and refractory multiple myeloma.

Studies of boronic acid protease inhibitors have been greatly advanced by the development of chemistry for the preparation of functionalized boronic add compounds, particularly alpha-halo- and alpha-aminoboronic acids. Matteson and Majumdar, *J. Am. Chem. Soc.*, 102:7558 (1950), discloses a method for preparing alpha-chloroboronic esters by homologation of boronic esters, and Matteson and Ray, *J. Am. Chem. Soc.*, 102:7590 (1980), reports that chiral control of the homologation reaction can be achieved by the use of pinanediol boronic esters. The preparation of alpha-aminoboronic acid and ester compounds from the corresponding alpha-chloroboronic esters has also been reported (Matteson et al., *J. Am. Chem. Soc.*, 103:5241 (1981); Shenvi, U.S. Pat. No. 4,537,773 (1985)).

Matteson and Sadhu, U.S. Pat. No. 4,525,309 (1985), describes an improved procedure for the homologation of boronic esters by rearrangement of the intermediate boron "ate" complex in the presence of a Lewis acid catalyst. The Lewis acid is reported to promote the rearrangement reaction and to minimize epimerization at the alpha-carbon atom. Rigorous exclusion of water and careful control of Lewis acid stoichiometry are required for optimum results, however. These features render the reaction difficult to perform successfully on a production scale, and limit the availability of pharmaceutically important boronic ester and acid compounds, such as bortezomib. Thus, there remains a need in the art for improved methods for the large-scale production of boronic ester and acid compounds.

DESCRIPTION OF THE INVENTION

The present invention provides improved synthetic processes for the large-scale production of boronic ester and acid compounds. These processes offer increased yield and purity, increased throughput, and greater ease of handling as compared to prior art methods. Notably, the processes described herein are suitable for batch production on a large, multi-kilogram scale that is limited only by the size of the available manufacturing capabilities. The processes of the invention are particularly advantageous for the synthesis of chiral boronic ester and acid compounds, including alpha-aminoboronic ester and acid compounds. Regardless of scale, the desired products are produced with very high chemical and stereochemical purity.

The patent and scientific literature referred to herein establishes knowledge that is available to those with skill in the art. Unless otherwise defined, all technical and scientific terms used herein have the same meaning as commonly understood by one of ordinary skill in the art to which this invention relates. Although methods and materials similar or equivalent to those described herein can be used in the practice or testing of the present invention, the preferred methods and materials are described herein. The issued patents, applications, and references that are cited herein are hereby incorporated by reference to the same extent as if each was specifically and individually indicated to be incorporated by reference. In the case of inconsistencies, the present disclosure, including definitions, will control. In addition, the materials, methods, and examples are illustrative only and are not intended to be limiting.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "comprises" is used herein to mean "includes, but is not limited to."

The term "aliphatic", as used herein, means a straight-chain, branched or cyclic $C_{1-12}$ hydrocarbon which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cylcoalkyl)alkyl, (cycloalkenyl)alkyl or (cycloalkyl)alkenyl. In various embodiments, the aliphatic group has 1-12, 1-8, 1-6, or 1-4 carbons.

The terms "alkyl", "alkenyl", and "alkynyl", used alone or as part of a larger moiety, refer to a straight and branched chain aliphatic group having from 1 to 12 carbon atoms, which is optionally substituted with one, two or three substituents. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl. For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The terms "cycloalkyl", "carbocycle", "carbocyclyl", "carbocyclo", or "carbocyclic", used alone or as part of a larger moiety, means a saturated or partially unsaturated cyclic aliphatic ring system having from 3 to about 14 members, wherein the aliphatic ring system is optionally substituted. Cycloalkyl groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloalkyl", "carbocycle", "carbocyclyl", "carbocyclo", or "carbocyclic" also include aliphatic rings that are fused to one or more aromatic or nonaromatic rings, such as decahydronaphthyl or tetrahydronaphthyl, where the radical or point of attachment is on the aliphatic ring.

The terms "haloalkyl", "haloalkenyl" and "haloalkoxy" refer to an alkyl, alkenyl or alkoxy group, as the case may be, substituted with one or more halogen atoms. As used herein, the term "halogen" or "halo" means F, C, Br, or I. Unless otherwise indicated, the terms "alkyl", "alkenyl", and "alkoxy" include haloalkyl, haloalkenyl and haloalkoxy groups, including, in particular, those with 1-5 fluorine atoms.

The terms "aryl" and "ar-", used alone or as part of a larger moiety, e.g., "aralkyl", "aralkoxy", or "aryloxyalkyl", refer to a $C_{6-14}$ aromatic moiety comprising one to three aromatic rings, which are optionally substituted. Preferably, the aryl group is a $C_{1-10}$ aryl group. Aryl groups include, without limitation, phenyl, naphthyl, and anthracenyl. The term "aryl", as used herein, also includes groups in which an aromatic ring is fused to one or more non-aromatic rings, such as indanyl, phenanthridinyl, or tetrahydronaphthyl, where the radical or point of attachment is on the aromatic ring. The term "aryl" may be used interchangeably with the term "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms selected from the group consisting of N, O, and S. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolyl, isoindolyl, benzothienyl, benzofuranyl, dibenzofuranyl, indazolyl, benzimidazolyl, benzthiazolyl, purinyl, quinolyl, isoquinolyl, cinnolinyl, phthalazinyl, quinoxalinyl, naphthyridinyl, pteridinyl, carbazolyl, acridinyl, and phenazinyl. The terms "heteroaryl" and "heteroar-", as used herein, also include groups in which a heteroaromatic ring is fused to one or more nonaromatic rings, where the radical or point of attachment is on the heteroaromatic ring. Nonlimiting examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", or "heterocyclic radical" refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms selected from the group consisting of N, O, and S, wherein the nitrogen and sulfur heteroatoms are optionally oxidized and the nitrogen atoms are optionally quaternized. The heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, and morpholinyl. The terms "heterocycle", "heterocyclyl", and "heterocyclic radical", as used herein, also include groups in which a non-aromatic heteroatom-containing ring is fused to one or more aromatic or non-aromatic rings, such as indolinyl, chromanyl, phenanthridinyl, or tetrahydroquinolinyl, where the radical or point of attachment is on the non-aromatic heteroatom-containing ring. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having one or multiple sites of unsaturation, but is not intended to include aryl or heteroaryl moieties, as herein defined.

The term "substituted", as used herein, means that one or more hydrogen atoms of the designated moiety are replaced, provided that the substitution results in a stable or chemically feasible compound. A stable compound or chemically feasible compound is one in which the chemical structure is not substantially altered when kept at a temperature of 40° C. or less, in the absence of moisture or other chemically reactive conditions, for at least a week, or a compound which maintains its integrity long enough to be useful for the synthetic processes of the invention. The phrase "one or more substituents", as used herein, refers to a number of substituents that equals from one to the maximum number of substituents possible based on the number of available bonding sites, provided that the above conditions of stability and chemical feasibility are met.

An aryl (including the aryl moiety in aralkyl, aralkoxy, aryloxyalkyl and the like) or heteroaryl (including the heteroaryl moiety in heteroaralkyl and heteroarylalkoxy and the like) group may contain one or more substituents. Examples of suitable substituents on the unsaturated carbon atom of an aryl or heteroaryl group include -halo, —$NO_2$, —CN, —R*, —OR*, —SR°, —$N(R^+)_2$, —$NR^+C(O)R^*$, —$NR^+C(O)N(R^+)_2$, —$NR^+CO_2R°$, —O—$CO_2R^*$, —O—$C(O)R^*$, —$CO_2R^*$, —C(O)R*, —$C(O)N(R^+)_2$, —$OC(O)N(R^+)_2$, —$S(O)_2R°$, —$SO_2N(R^+)_2$, —S(O)R°, and —$NR^+SO_2N(R^+)_2$. Each $R^+$ independently is selected from the group consisting of R*, —C(O)R*, —$CO_2R^*$, and —$SO_2R^*$, or two $R^+$ on the same nitrogen atom, taken together with the nitrogen atom, form a 5-8 membered aromatic or non-aromatic ring having, in addition to the nitrogen, 0-2 ring heteroatoms selected from N, O, and S. Each R* independently is hydrogen or an optionally substituted aliphatic, aryl, heteroaryl, or heterocyclyl group. Each R° independently is an optionally substituted aliphatic or aryl group.

An aliphatic group also may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group.

The present inventors have discovered that the requirement for scrupulously dry equipment, solvents, and reagents that characterized previously described procedures for the Lewis acid promoted rearrangement of boron "ate" complexes can be obviated by use of an ether solvent that has low miscibility with water. Remarkably, use of such a solvent permits the reaction to be run on a multi-kilogram scale without deterioration in yield or purity. In essence, the scale of the reaction is limited only by the size of the available manufacturing capabilities.

In one aspect, therefore, the invention provides a large-scale process for preparing a boronic ester compound of formula (I):

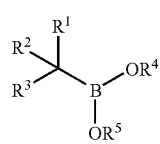

wherein:
  $R^1$ is an optionally substituted aliphatic, aromatic, or heteroaromatic group;
  $R^2$ is hydrogen, a nucleofugic group, or an optionally substituted aliphatic, aromatic, or heteroaromatic group;
  $R^3$ is a nucleofugic group or an optionally substituted aliphatic, aromatic, or heteroaromatic group; and
  each of $R^4$ and $R^5$, independently, is an optionally substituted aliphatic, aromatic, or heteroaromatic group, or $R^4$ and $R^5$, taken together with the intervening oxygen and boron atoms, form an optionally substituted 5- to 10-membered ring having 0-2 additional ring heteroatoms selected from N, O, or S.

The process comprises the steps:
(a) providing a boron "ate" complex of formula (II):

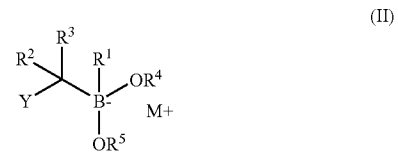

where
  Y is a nucleofugic group;
  $M^+$ is a cation; and
  each of $R^1$ to $R^5$ is as defined above; and
(b) contacting the boron "ate" complex of formula (II) with a Lewis acid under conditions that afford the boronic ester compound of formula (I), said contacting step being conducted in a reaction mixture comprising:
  (i) a coordinating ether solvent that has low miscibility with water; or
  (ii) an ether solvent that has low miscibility with water and a coordinating co-solvent.

The previously reported processes for Lewis acid promoted rearrangement of boron "ate" complexes employ tetrahydrofuran, an ether solvent that is fully miscible with water. Failure to employ rigorously dried equipment, solvents, and reagents in these processes results in a dramatic reduction in the diastereomeric ratio. The hygroscopic Lewis acids, in particular, typically must be flame-dried immediately prior to use in the reaction. Although techniques for running moisture-sensitive reactions are familiar to those of skill in the art and are routinely practiced on a laboratory scale, such reactions are costly and difficult to scale up.

Moreover, attempted scale-up of the prior art process frequently results in a further deterioration in diastereomeric ratio during workup and isolation of the product boronic ester compound. Matteson and Erdiik, *Organometallics,* 2:1083 (1983), reports that exposure of alpha-haloboronic ester products to free halide ion results in epimerization at the alpha-carbon center. Without wishing to be bound by theory, the present inventors believe that epimerization is particularly problematic during reaction work-up and/or subsequent steps. For example, epimerization is believed to occur during concentration of the reaction mixture to remove the tetrahydrofuran solvent and exchange it for a water-immiscible solvent. Failure to completely remove the tetrahydrofuran also negatively impacts diastereomeric ratio during the subsequent aqueous washes. Exposure of the product to halide ion during these steps is difficult to avoid, particularly when the reaction is performed on a large scale.

The present inventors have discovered that the rearrangement of boron "ate" complexes is advantageously performed in an ether solvent that has low miscibility with water. Use of such solvents obviates the need for solvent exchange prior to the aqueous washes, and the organic-soluble product is effectively shielded from aqueous halide ion during the washes, even if performed on a large scale. Preferably, the solubility of water in the ether solvent is less than about 5% w/w, more preferably less than about 2% w/w. In various embodiments, ether solvent that has low miscibility with water constitutes at least about 70%, at least about 80%, at least about 85%, at least about 90%, or at least about 95% v/v of the reaction mixture.

The ether solvent preferably is one that is suitable for routine use in large-scale production. As used herein, the term "large-scale" refers to a reaction that utilizes at least about five moles of at least one starting material. Preferably, a large-scale process utilizes at least about 10, 20, 50, or 100 moles of at least one starting material.

For purposes of the invention, the term "ether" refers to any of a class of chemical compounds characterized in having an oxygen atom attached to two carbon atoms. An "ether solvent" is an ether compound that exists in liquid form at the desired reaction temperature and is capable of dissolving the starting material(s) and/or product(s) of the reaction. Nonlimiting examples of ether solvents suitable for use in the process of the invention include tert-butyl methyl ether, tert-butyl ethyl ether, tert-amyl methyl ether, and isopropyl ether.

In one embodiment, the reaction mixture further comprises a coordinating co-solvent. In another embodiment, the ether solvent that has low miscibility with water is sufficiently coordinating that a coordinating co-solvent is not necessary. For purposes of the invention, the terms "coordinating co-solvent" and "coordinating solvent" refer to a solvent that is capable of coordinating the Lewis acid and solvating the ionic components of the reaction. Hindered ether solvents, such as tert-butyl methyl ether, are poorly coordinating and preferably are used with a coordinating co-solvent. Nonlimiting examples of coordinating co-solvents suitable for use in the practice of the invention include tetrahydrofuran, dioxane, water, and mixtures thereof.

In some embodiments, the reaction mixture comprises at least about 5% or at least about 10% v/v of a coordinating co-solvent. Preferably, the amount of a water-miscible coordinating co-solvent present in the reaction mixture is not so great as to interfere with phase separation during the reaction or workup. In various embodiments, the coordinating co-solvent constitutes no more than about 20%, about 15%, or about 10% v/v of the reaction mixture.

As used herein, the term "nucleofugic" refers to any group that is capable of undergoing nucleophilic displacement under the rearrangement conditions of the present process. Such nucleofugic groups are known in the art. Preferably, the nucleofugic group is a halogen, more preferably chloro or bromo. In the course of the rearrangement reaction converting the boron "ate" complex of formula (II) into the boronic ester compound of formula (I), the nucleofugic group Y is released as $Y^-$. By way of example, when Y is chloro, chloride ion is released in step (b).

The variable $M^+$ is any cationic counterion for the negatively charged tetravalent boron atom in the boron "ate" complex of formula (II). In some preferred embodiments, $M^+$ is selected from the group consisting of $Li^+$, $Na^+$, and $K^+$. One of skill in the art will recognize that the salt $M^+Y^-$ is formed as a byproduct in the rearrangement reaction of step (b).

The variable $R^1$ preferably is a group with good migratory aptitude. In some embodiments, $R^1$ is $C_{1-8}$ aliphatic, $C_{6-10}$ aryl, or $(C_{6-10}$ aryl$)(C_{1-6}$ aliphatic), any of which groups is optionally substituted. In certain embodiments, $R^1$ is $C_{1-4}$ aliphatic, particularly isobutyl.

The variable $R^2$ preferably is hydrogen, a nucleofugic group, or an optionally substituted $C_{1-8}$ aliphatic, $C_{6-10}$ aryl, or $(C_{6-10}$ aryl$)(C_{1-6}$ aliphatic) group. The variable $R^3$ preferably is a nucleofugic group or an optionally substituted $C_{1-8}$ aliphatic, $C_{6-10}$ aryl, or $(C_{6-10}$ aryl$)(C_{1-6}$ aliphatic) group. One of skill in the art will recognize that functional substituents may be present on any of $R^1$, $R^2$, or $R^3$, provided that the functional substituent does not interfere with the formation of the boron "ate" complex of formula (II).

One embodiment of the invention relates to a process for preparing a boronic ester compound of formula (I), wherein $R^3$ is a nucleofugic group. Such compounds are useful as intermediates for the synthesis of alpha-substituted boronic ester and acid compounds, including alpha-aminoboronic ester and acid compounds, as described below. In certain preferred embodiments, $R^3$ is a nucleofugic group and $R^2$ is hydrogen.

The variables $R^4$ and $R^5$ can be the same or different. In some embodiments, $R^4$ and $R^5$ are directly linked, so that $R^4$ and $R^5$, taken together with the intervening oxygen and boron atoms, form an optionally substituted 5- to 10-membered ring, which can have 0-2 additional ring heteroatoms selected from N, O, or S. In some embodiments, the ring is a 5- or 6-membered ring, preferably a 5-membered ring.

The present invention is particularly advantageous for the Lewis acid promoted rearrangement of boron "ate" complexes of formula (II), wherein $R^4$ and $R^5$ are directly linked and together are a chiral moiety. One embodiment of the invention relates to the rearrangement of such chiral boron "ate" complexes to provide a boronic ester compound of formula (I) wherein the carbon atom bearing $R^1$, $R^2$, and $R^3$ is a chiral center. The rearrangement reaction preferably proceeds with a high degree of stereodirection by the $R^4$—$R^5$ chiral moiety to provide the boronic ester compound of formula (I) having a diastereomeric ratio at the carbon atom bearing $R^1$, $R^2$, and $R^3$ of at least about 96:4 relative to a chiral center in the $R^4$—$R^5$ chiral moiety. Preferably, the diastereomeric ratio is at least about 97:3.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer=(R*R+S*S):(R*S+S*R).

One of ordinary skill in the art will recognize that additional stereoisomers are possible when the molecule has more than two chiral centers. For purposes of the present invention, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diasteromeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (BPLC) methods.

As discussed above, one embodiment of the invention is directed to processes that provide a boronic ester compound of formula (I) having a diastereomeric ratio at the carbon atom bearing $R^1$, $R^2$, and $R^3$ of at least about 96:4 relative to a chiral center in the $R^4$—$R^5$ chiral moiety. One of skill in the art will recognize that the $R^4$—$R^5$ chiral moiety may itself contain more than one chiral center. When $R^4$—$R^5$ does have more than one chiral center, it preferably has high diastereomeric purity, and the diastereomeric ratio at the carbon atom bearing $R^1$, $R^2$, and $R^3$ can be measured relative to any one of the chiral centers in $R^4$—$R^5$.

In the processes of the invention, the $R^4$—$R^5$ chiral moiety preferably has a high level of enantiomeric purity. For purposes of the invention, the term "enantiomeric purity" is used to mean "enantiomeric excess", which is the amount by which the major enantiomer is in excess of the minor enantiomer, expressed as a percentage of the total. Preferably, the $R^4$—$R^5$ chiral moiety has an enantiomeric purity of at least about 98%, more preferably at least about 99%, still more preferably at least about 99.5%, and most preferably at least about 99.9%.

When the $R^4$—$R^5$ chiral moiety has very high enantiomeric purity, the diastereomeric ratio at the carbon atom bearing $R^1$, $R^2$, $R^3$ approximates the epimeric ratio at that center, i.e., diastereomeric ratio≅(R*R):(S*R) or (R*S):(S*S)≅(R*):(S*). As used herein, the term "epimeric ratio" refers to the ratio of product having one absolute stereochemical configuration at a given chiral center to product having the opposite absolute stereochemical configuration at the corresponding chiral center. Preferably, the products have identical stereochemical configuration at all other corresponding chiral centers. In one embodiment, therefore, the invention relates to the rearrangement of a chiral boron "ate" complex of formula (II) to provide a boronic ester compound of formula (I) wherein the epimeric ratio at the carbon atom bearing $R^1$, $R^2$, and $R^3$ is at least about 96:4, more preferably at least about 97:3.

Lewis acids suitable for use in the practice of the invention are those capable of complexing with the nucleofugic group to facilitate its displacement upon migration of $R^1$. Preferably, the Lewis acid is additionally capable of coordinating with an oxygen atom attached to boron. Nonlimiting examples of suitable Lewis acids include zinc bromide, zinc chloride, ferric bromide, and ferric chloride. In certain preferred embodiments, the Lewis acid is zinc chloride.

The contacting step preferably is performed at low temperature, but may be performed at ambient or elevated temperature. The selection of an appropriate reaction temperature will depend largely on the Lewis acid employed, as well as the migratory aptitude of the $R^1$ moiety. One skilled in the art will be able to select a suitable temperature in view of the reaction conditions being used.

In some embodiments, the contacting step is performed at a reaction temperature of at least about −100° C., −78° C., or −60° C. In some embodiments, the contacting step is performed at a reaction temperature that is no greater than about 80° C., 40° C., or 30° C. Any range encompassing these high and low temperatures are included within the scope of the invention. Preferably, the contacting step is performed at a reaction temperature in the range of about −100° C. to about 80° C., about −70° C. to about 40° C., about −60° C. to about 30° C., or about −50° C. to about 30° C. In certain preferred embodiments, the contacting step is begun at low temperature, preferably in the range of about −70° C. to about −30° C., and then the reaction mixture is allowed to warm, preferably to ambient temperature.

Surprisingly, the process of the present invention requires no special precautions to avoid the presence of water during the rearrangement reaction itself. In some embodiments, moist Lewis acid is employed, with minimal deterioration in diastereomeric ratio. When used in reference to the Lewis acid, the term "moist" means that the water content of the Lewis acid is greater than about 100, 200, 500, or 1,000 ppm. Remarkably, the Lewis acid even can be added to the reaction mixture in the form of an aqueous solution without deleterious impact on diastereomeric ratio.

In some embodiments, therefore, the process of the invention comprises the steps:
(a) providing a solution comprising a boron "ate" complex of formula (II) and
  (i) a coordinating ether solvent that has low miscibility with water; or
  (ii) an ether solvent that has low miscibility with water and a coordinating co-solvent; and
(b) adding to the solution of step (a) a Lewis acid solution comprising water and a Lewis acid.

In some other embodiments, the Lewis acid solution comprises tetrahydrofuran and a Lewis acid.

Thus, unlike the prior art process, the process of the invention is readily amenable to large-scale production. In various embodiments, at least about 5, 10, 20, 50, 100, 500, or 1000 moles of boron "ate" complex of formula (II) is contacted with a Lewis acid under conditions that afford the boronic ester compound of formula (I). The invention further provides a composition comprising a boronic ester compound of formula (I), as described herein, and an ether solvent that has low miscibility with water. The composition preferably comprises at least about 5, 10, 20, 50, 100, 500, or 1000 moles of the boronic ester compound of formula (I). In certain embodiments, $R^4$ and $R^5$ together are a chiral moiety, and the compound of formula (I) present in the composition has a diastereomeric ratio of at least about 96:4 at the carbon atom bearing $R^1$, $R^2$, and $R^3$, relative to a chiral center in the $R^4$—$R^5$ chiral moiety.

Workup of the reaction preferably comprises washing the reaction mixture with an aqueous solution and concentrating the washed reaction mixture by removal of solvents to afford a residue comprising the boronic ester compound of formula (I). Preferably, the residue comprises at least about 5, 10, 20, 50, 100, 500, or 1000 moles of the boronic ester compound of formula (I). In those embodiments wherein $R^4$—$R^5$ is a chiral moiety, the boronic ester compound of formula (I) present in the residue preferably has a diastereomeric ratio of at least about 96:4 at the carbon atom bearing $R^1$, $R^2$, and $R^3$, relative to a chiral center in the $R^4$—$R^5$ chiral moiety. More preferably, the diastereomeric ratio is at least about 97:3.

The boron "ate" complex of formula (II) can be prepared by any known method, but preferably is prepared by reaction of a boronic ester of formula (III):

(III)

with a reagent of formula (IV):

(IV)

wherein each of $M^+$, Y, and $R^1$ to $R^5$ are as defined above for the boron "ate" complex of formula (II). In some embodiments, the reaction is performed at a reaction temperature of at least about −100° C., −78° C., or −60° C. In some embodiments, the reaction is performed at a reaction temperature no greater than about 0° C., −20° C., or −40° C. Any range encompassing these high and low temperatures are included within the scope of the invention. The reaction preferably is performed at a reaction temperature in the range of about −100° C. to about 0° C., about −78° C. to about −20° C., or about −60° C. to about −40° C. In some embodiments, the boron "ate" complex of formula (II) is prepared in a solution comprising an ether solvent having low miscibility with water, and the reaction mixture is directly treated with a Lewis acid to effect rearrangement to the boron ester compound of formula (I).

In some embodiments, the reagent of formula (IV) is formed in situ. Such embodiments include the steps:

(i) providing a solution comprising a boronic ester of formula (III), as defined above, and a compound of formula (V):

(V)

wherein $R^2$ and $R^3$ are as defined above for the reagent of formula (IV); and (ii) treating the solution with a strong, sterically hindered base to form the boron "ate" complex of formula (II).

In some embodiments, the sterically hindered base is an alkali metal dialkylamide bases of formula $M^2N(R^\#)_2$, where $M^2$ is Li, Na, or K, and each $R^\#$, independently is a branched or cyclic $C_{3-6}$ aliphatic. In situ formation of the reagent of formula (IV) is especially advantageous in those embodiments wherein Y is a nucleofugic group, due to the instability of the reagent of formula (IV).

The boronic ester of formula (III) can be prepared by any known method, but typically is prepared by esterification of the corresponding boronic acid compound, e.g., by methods described in Brown et al., *Organometallics*, 2: 1311-1316 (1983). Cyclic boronic esters of formula (III) preferably are prepared by:

(a) providing a solution comprising:
  (i) a boronic acid compound of formula $R^1$—$B(OH)_2$;
  (ii) a compound of formula HO—$R^4$—$R^5$—OH, wherein $R^4$ and $R^5$, taken together, are an optionally substituted linking chain comprising 2-5 carbon atoms and 0-2 heteroatoms selected from the group consisting of O, N, and S; and
  (iii) an organic solvent that forms an azeotrope with water; and (b) heating the solution at reflux with azeotropic removal of water.

As used in reference to $R^4$ and $R^5$, the term "linking chain" refers to the shortest linear chain of atoms connecting the oxygen atoms to which $R^4$ and $R^5$ are attached. The linking chain optionally is substituted at any chain atom, and one or more chain atoms also may form part of a ring system that is spiro to, fused to, or bridging the linear linking chain. By way of example, but not limitation, in some embodiments, the compound of formula HO—$R^4$—$R^5$—OH is pinanediol, having the structure:

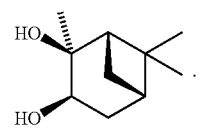

In such embodiments, the linking chain $R^4$—$R^5$ comprises two carbon atoms, which together form one side of the bicyclo[3.1.1]heptane ring system, and one of which additionally is substituted with a methyl group.

In some embodiments, the compound of formula HO—$R^4$—$R^5$—OH is a chiral diol, preferably one having high diastereomeric and enantiomeric purity. One of skill in the art will appreciate that in such embodiment, the compound of formula HO—$R^4$—$R^5$—OH is employed as a chiral auxiliary to direct the stereochemical configuration at the carbon bearing $R^1$, $R^2$, and $R^3$. Chiral diols useful as chiral auxiliaries in organic synthesis are well-known in the art. Nonlimiting examples include 2,3-butanediol, preferably (2R,3R)-(−)-2,3-butanediol or (2S,3S)-(+)-2,3-butanediol; pinanediol, preferably (1R,2R,3R,5S)-(−)-pinanediol or (1S,2S,3S,5R)-(+)-pinanediol; 1,2-cyclopentanediol, preferably (1S,2S)-(+)-trans-1,2-cyclopentanediol or (1R,2R)-(−)-trans-1,2-cyclopentanediol; 2,5-hexanediol, preferably (2S,5S)-2,5-hexanediol or (2R,5R)-2,5-hexanediol; 1,2-dicyclohexyl-1,2-ethanediol, preferably (1R,2R)-1,2-dicyclohexyl-1,2-ethanediol or (1S,2S)-1,2-dicyclohexyl-1,2-ethanediol; hydrobenzoin, preferably (S,S)-(−)-hydrobenzoin or (R,R)-(+)-hydrobenzoin; 2,4-pentanediol, preferably (R,R)-(−)-2,4-pentanediol or (S,S,)-(+)-2,4-pentanediol; erythronic γ-lactone, preferably D-erythronic γ-lactone. Carbohydrates, e.g. a 1,2,5,6-symmetrically protected mannitol, also may be used as chiral diols.

Nonlimiting examples of organic solvents suitable for use in the esterification reaction include acetonitrile, toluene, hexane, heptane, and mixtures thereof. In some embodiments, the organic solvent is an ether solvent, preferably an ether solvent that has low miscibility with water. In certain preferred embodiments, the esterification reaction is performed in an ether solvent that has low miscibility with water, and the product solution comprising the boronic ester of formula (III) is used directly in the next step, without isolation of the boronic ester.

As noted above, the process of the present invention for the first time permits workup of large-scale reactions without significant deterioration in diastereomeric ratio. In another aspect, therefore, the invention provides a composition comprising at least about 5, 10, 20, 50, 100, 500, or 1000 moles of a boronic ester compound of formula (I):

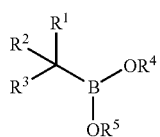

(I)

wherein:
- $R^1$ is an optionally substituted aliphatic, aromatic, or heteroaromatic group;
- $R^2$ is hydrogen, a nucleofugic group, or an optionally substituted aliphatic, aromatic, or heteroaromatic group;
- $R^3$ is a nucleofugic group or an optionally substituted aliphatic, aromatic, or heteroaromatic group; and
- $R^4$ and $R^5$, taken together with the intervening oxygen and boron atoms, form an optionally substituted 5- to 10-membered chiral ring having 0-2 additional ring heteroatoms selected from N, O, or S;
- wherein the carbon atom to which $R^1$, $R^2$, and $R^3$ are attached is a chiral center, having a diastereomeric ratio of at least about 96:4, preferably at least about 97:3, relative to a chiral center in the $R^4$—$R^5$ chiral moiety.

Preferred values for $R^1$ to $R^3$ are as described above. Preferably, solvents constitute less than about 30% w/w, 20% w/w, 10% w/w, or 5% w/w of the composition according to this aspect of the invention. In some embodiments, the boronic ester compound of formula (I) constitutes at least about 70% w/w, 80% w/w, 90% w/w, or 95% w/w of the composition.

One embodiment relates to the composition described above, wherein at least one of the following features is present:
(a) $R^3$ is chloro;
(b) the boronic ester compound (I) is

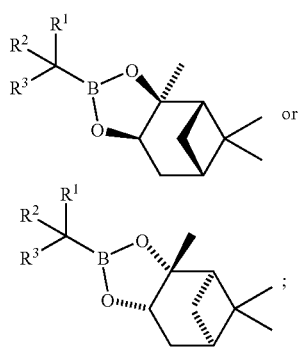

(c) $R^2$ is hydrogen; and
(d) $R^1$ is $C_{1-4}$ aliphatic.

All of the boronic ester compound of formula (I) present in the composition may be produced in a single batch run. For purposes of the invention, the term "batch run" refers to execution of a synthetic process, wherein each step of the process is performed only once. Preferably, the boronic ester compound of formula (I) present in the composition is prepared in a single batch run of the process according to the first aspect of the invention. One of ordinary skill in the art will appreciate that preparation of a given quantity of product by a single batch run of a large-scale process is more efficient and provides a more homogeneous product than preparation of the same quantity of product by repeated execution of a small-scale process.

The boronic ester compounds of formula (I) wherein $R^3$ is a nucleofugic group are useful as intermediates for the synthesis of alpha-aminoboronic ester compounds. In another aspect, therefore, the invention provides a large-scale process for preparing an alpha-aminoboronic ester, preferably by a process comprising the steps:
(a) providing a boron "ate" complex of formula (II):

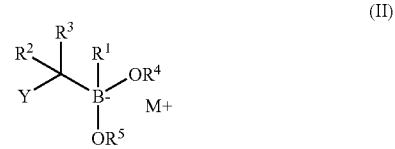

(II)

where
- Y is a nucleofugic group;
- $M^+$ is a cation;
- $R^1$ is an optionally substituted aliphatic, aromatic, or heteroaromatic group;
- $R^2$ is hydrogen;
- $R^3$ is a nucleofugic group; and
- each of $R^4$ and $R^5$, independently, is an optionally substituted aliphatic, aromatic, or heteroaromatic group, or $R^4$ and $R^5$, taken together with the intervening oxygen and boron atoms, form an optionally substituted 5- to 10-membered ring having 0-2 additional ring heteroatoms selected from N, O, or S;

(b) contacting the boron "ate" complex of formula (II) with a Lewis acid under conditions that afford the boronic ester compound of formula (I):

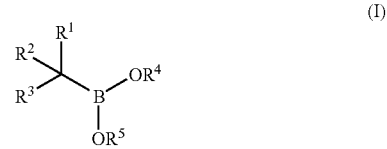

(I)

where each of $R^1$ to $R^5$ is as defined above, said contacting step being conducted in a reaction mixture comprising:
(i) a coordinating ether solvent that has low miscibility with water; or
(ii) an ether solvent that has low miscibility with water and a coordinating co-solvent; and (c) treating the boronic ester compound of formula (I) with a reagent of formula $M^1$-$N(G)_2$, where $M^1$ is an alkali metal and each G individually or together is an amino group protecting group to form a byproduct of formula $M^1$-$R^3$ and a compound of formula (VIII):

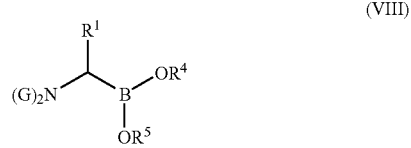

(VIII)

wherein each G and $R^1$ to $R^5$ are as defined above; and
(d) removing the G groups to form a compound of formula (VII):

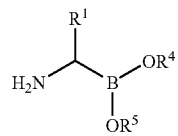
(VII)

or an acid addition salt thereof.

In some embodiments, in step (c), the boronic ester compound of formula (I) is treated with a reagent of formula $M^1$-$N(Si(R^6)_3)_2$ where $M^1$ is an alkali metal and each $R^6$ independently is selected from the group consisting of alkyl, aralkyl, and aryl, where the aryl or aryl portion of the aralkyl is optionally substituted.

Reaction of the boronic ester compound of formula (I) with the reagent of formula $M^1$-$N(G)_2$ preferably is conducted at a reaction temperature in the range of about −100° C. to about 50° C., preferably about −50° C. to about 25° C., and more preferably about −30° C. to about 0° C. In some embodiments, $R^3$ is halo, preferably chloro, and $M^1$ is Li. To facilitate isolation of the product of formula (VIII), the reaction mixture preferably comprises an organic solvent in which the byproduct $M^1$-$R^3$ has low solubility. Nonlimiting examples of suitable organic solvents include methylcyclohexane, cyclohexane, heptane, hexane, and toluene. In some embodiments, step (c) further comprises filtering the reaction mixture to remove $M^1$-$R^3$ and provide a filtrate comprising the compound of formula (VIII). Preferably, the filtrate is used directly in step (d).

In those embodiments wherein the reaction mixture comprises an organic solvent in which the byproduct $M^1$-$R^3$ has low solubility, the reaction mixture may additionally comprise a solvent in which the byproduct $M^1$-$R^3$ has high solubility. In such cases, the solvent in which the byproduct $M^1$-$R^3$ has high solubility preferably is removed prior to filtration of the reaction mixture. By way of example, in some embodiments, a reagent of formula $M^1$-$N(Si(R^6)_3)_2$ is added to the reaction mixture as a solution comprising tetrahydrofuran. In such embodiments, step (c) preferably further comprises removing the tetrahydrofuran before filtering the reaction mixture.

Those of skill in the art are aware of various methods that can be used to remove the protecting groups G in the compound of formula (VIII), including, e.g., aqueous hydrolysis or treatment with acid. The product alpha-aminoboronic ester of formula (VII) has low stability and preferably is immediately derivatized (Matteson et al., *J. Am. Chem. Soc.*, 103: 5241 (1981)) or is isolated as an acid addition salt. In some embodiments, step (d) comprises treating the compound of formula (VIII) with an acid and isolating the compound of formula (VII) as the acid addition salt. In certain preferred embodiments, the acid is trifluoroacetic acid, and the compound of formula (VII) is isolated as the trifluoroacetic acid addition salt.

As discussed above, the processes of the invention are particularly well-suited for preparing alpha-aminoboronic ester compounds of formula (VII), wherein the alpha carbon is a chiral center. Thus, one embodiment of the invention relates to a large-scale process for preparing an alpha-aminoboronic ester compound of formula (VIIa) or (VIIb):

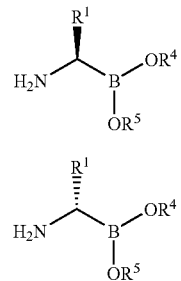
(VIIa)

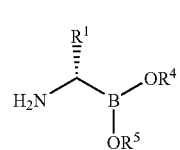
(VIIb)

or an acid addition salt thereof, wherein:
$R^1$ is an optionally substituted aliphatic, aromatic, or heteroaromatic group; and
$R^4$ and $R^5$, taken together with the intervening oxygen and boron atoms, form an optionally substituted chiral cyclic boronic ester;

said process comprising:
(a) providing a boron "ate" complex of formula (IIa) or (IIb):

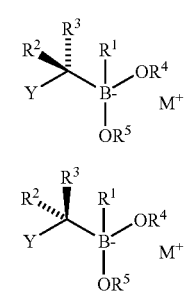
(IIa)

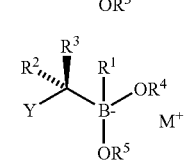
(IIb)

where
Y is a nucleofugic group;
$M^+$ is a cation;
$R^2$ is hydrogen;
$R^3$ is a nucleofugic group; and
$R^4$ and $R^5$ are as defined above;
(b) contacting the boron "ate" complex of formula (IIa) or (IIb) with a Lewis acid under conditions that afford a boronic ester compound of formula (Ia) or (Ib):

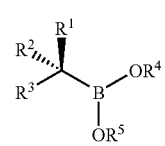
(Ia)

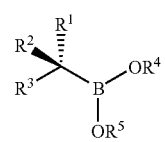
(Ib)

where each of $R^1$ to $R^5$ is as defined above, said contacting step being conducted in a reaction mixture comprising:

(i) a coordinating ether solvent that has low miscibility with water; or
(ii) an ether solvent that has low miscibility with water and a coordinating co-solvent; and
(c) treating the boronic ester compound of formula (Ia) or (Ib) with a reagent of formula $M^1$-$N(G)_2$, where $M^1$ is an alkali metal and G is an amino group protecting moiety, to form a compound of formula (VIIIa) or (VIIIb):

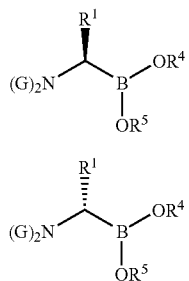

(VIIIa)

(VIIIb)

wherein each G and $R^1$ to $R^5$ are as defined above; and
(d) removing the G groups to form a compound of formula (VIIa) or (VIIb):

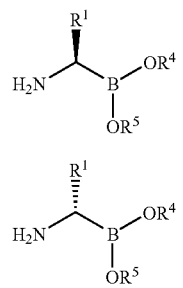

(VIIa)

(VIIb)

or an acid addition salt thereof.

Preferred values for Y, $M^+$, $R^1$ to $R^5$, and G are as described above. The compound of formula (VIIa) or (VIIb) preferably has a diastereomeric ratio at the alpha-carbon of at least about 96:4, more preferably at least about 97:3, relative to a chiral center in the $R^4$—$R^5$ chiral moiety.

The alpha-aminoboronic ester compounds of formula (VII) are useful synthetic intermediates for the preparation of peptidyl boronic ester compounds. In some embodiments, therefore, the process according to this aspect of the invention further comprises coupling the compound of formula (VII) with a compound of formula (IX):

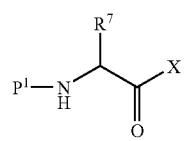

(IX)

wherein:
$P^1$ is an amino group blocking moiety;
$R^7$ is selected from the group consisting of hydrogen, $C_{1-10}$aliphatic, optionally substituted $C_{6-10}$aryl, or $C_{1-6}$aliphatic-$R^8$; and $R^8$ is selected from the group consisting of alkoxy, alkylthio, optionally substituted aryl, heteroaryl, and heterocyclyl groups, and optionally protected amino, hydroxy, and guanidino groups; and
X is OH or a leaving group;
to form a compound of formula (X):

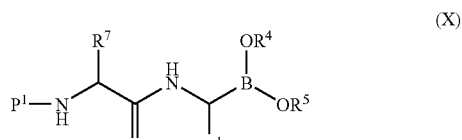

(X)

wherein each of $P^1$, $R^1$, $R^4$, $R^5$, and $R^7$ is as defined above.

The leaving group X is any group capable of nucleophilic displacement by the alpha-amino group of the compound of formula (VII). In some embodiments, the moiety —C(O)—X is an activated ester, such as an O—(N-hydroxysuccinimide) ester. In some embodiments, an activated ester is generated in situ by contacting a compound of formula (IX), wherein X is OH, with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., benzotriazol-1-yloxytris(dimethylamino)phosphonium hexafluorophosphate (BOP reagent); and uronium reagents, e.g., O-(1H-benzotriazol-1-yl)-N,N,N',N'-tetramethyluronium tetrafluoroborate (TBTU).

Those of skill in the art also are aware of procedures that permit the direct coupling of silyl protected amines, without a prior deprotection step. In such procedures, the silyl groups are removed in situ under the coupling reaction conditions. In some embodiments of the present invention, therefore, a compound of formula (VIII) is contacted with a compound of formula (IX) under conditions that remove the $(R^6)_3Si$ groups in situ and form a compound of formula (X).

For purposes of the invention, the term "amino-group blocking moiety" refers to any group used to derivatize an amino group, especially an N-terminal amino group of a peptide or amino acid. The term "amino-group blocking moiety" includes, but is not limited to, protecting groups that are commonly employed in organic synthesis, especially peptide synthesis. See, for example, Gross and Mienhoffer, eds., *The Peptides*, Vol. 3, Academic Press, New York, 1981, pp. 3-88; Green and Wuts, *Protective Groups in Organic Synthesis*, 3$^{rd}$ edition, John Wiley and Sons, Inc., New York, 1999. Unless otherwise specified, however, it is not necessary for an amino-group blocking moiety to be readily cleavable. Amino-group blocking moieties include, e.g., alkyl, acyl, alkoxycarbonyl, aminocarbonyl, and sulfonyl moieties. In some embodiments, the amino-group blocking moiety is an acyl moiety derived from an amino acid or peptide, or a derivative or analog thereof.

As used herein, the term "amino acid" includes both naturally occurring and unnatural amino acids. For purposes of the invention, a "derivative" of an amino acid or peptide is one in which a functional group, e.g., a hydroxy, amino, carboxy, or guanidino group at the N-terminus or on a side chain, is modified with a blocking group. As used herein, an "analog" of an amino acid or peptide is one which includes a modified backbone or side chain. The term "peptide analog" is intended to include peptides wherein one or more stereocenters are inverted and one or more peptide bonds are replaced with a peptide isostere.

In some embodiments, $P^1$ is a cleavable protecting group. Examples of cleavable protecting groups include, without limitation, acyl protecting groups, e.g., formyl, acetyl (Ac), succinyl (Suc), or methoxysuccinyl (MeOSuc), and urethane protecting groups, e.g., tert-butoxycarbonyl (Boc), benzyloxycarbonyl (Cbz), or fluorenylmethoxycarbonyl (Fmoc).

In some such embodiments, the process according to this aspect of the invention further comprises the steps:

(f) removing the protecting group $P^1$ to form a compound of formula (XI):

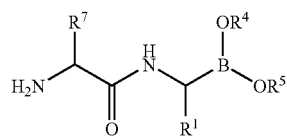

(XI)

or an acid addition salt thereof, wherein each of $R^1$, $R^4$, $R^5$, and $R^7$ is as defined above; and (g) coupling the compound of formula (XI) with a reagent of formula $P^2$—X, wherein $P^2$ is any amino group blocking moiety, as described above, and X is a leaving group, to form a compound of formula (XII):

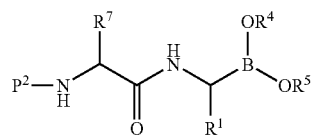

(XII)

wherein each of $P^2$, $R^1$, $R^4$, $R^5$, and $R^7$ are as defined above. One of skill in the art will recognize that in those embodiments wherein $P^2$ is an acyl group, including, e.g., an acyl moiety derived from an amino acid or peptide, or an analog or derivative thereof, the leaving group X may be generated in situ, as discussed above for the compound of formula (IX).

In each of the compounds (X) and (XII), the boronic acid moiety is protected as a boronic ester. If desired, the boronic acid moiety can be deprotected by any method known in the art. Preferably, the boronic acid moiety is deprotected by transesterification in a biphasic mixture. More preferably, the boronic acid deprotecting step comprises the steps:

(i) providing a biphasic mixture comprising the boronic ester compound of formula (X) or (XII), an organic boronic acid acceptor, a lower alkanol, a $C_{5-8}$ hydrocarbon solvent, and aqueous mineral acid;

(ii) stirring the biphasic mixture to afford the corresponding deprotected boronic acid compound of formula (Xa) or (XIII):

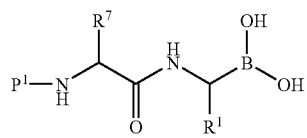

(Xa)

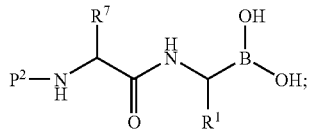

(XIII)

(iii) separating the solvent layers; and (iv) extracting the compound of formula (Xa), (XIII), or a boronic acid anhydride thereof, into an organic solvent.

The organic boronic acid acceptor in step (i) preferably is an aliphatic, aryl, or ar(aliphatic)boronic acid. In some embodiments, the boronic acid acceptor is selected from the group consisting of phenylboronic acid, benzylboronic acid, butylboronic acid, pentylboronic acid, hexylboronic acid, and cyclohexylboronic acid. In certain embodiments, the boronic acid acceptor is isobutylboronic acid. In some embodiments, the boronic acid acceptor is selected so that the boronic ester compound of formula (III) is formed as a byproduct of the deprotection reaction. The boronic ester compound of formula (III) can then be used in another batch run of the process described above. In such embodiments, the moiety $R^4$—$R^5$ is effectively recycled, which may be particularly advantageous if $R^4$—$R^5$ is an expensive chiral moiety.

To enhance the purity of the product, the aqueous layer containing the compound of formula (Xa) or (XIII) preferably is washed to remove neutral organic impurities prior to the extracting step (iv). In such embodiments, step (iii) preferably comprises the steps:

(1) separating the solvent layers;

(2) adjusting the aqueous layer to basic pH;

(3) washing the aqueous layer with an organic solvent; and (4) adjusting the aqueous layer to a pH less than about 6.

In some embodiments, the invention relates to an improved process for manufacturing the proteasome inhibitor bortezomib. Thus, in one embodiment, the invention provides a large-scale process for forming a compound of formula (XIV):

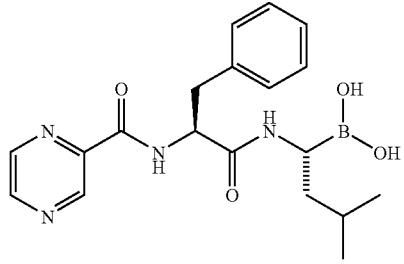

(XIV)

or a boronic acid anhydride thereof. The process comprises the steps:

(a) providing a boron "ate" complex of formula (XV):

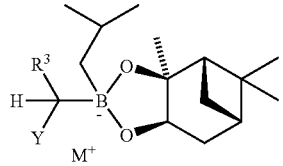

(XV)

wherein:

$R^3$ is a nucleofugic group;

Y is a nucleofugic group; and $M^+$ is an alkali metal;

(b) contacting the boron "ate" complex of formula (XV) with a Lewis acid under conditions that afford a boronic ester compound of formula (XVI):

(XVI)

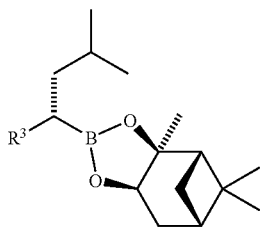

said contacting step being conducted in a reaction mixture comprising:
(i) a coordinating ether solvent that has low miscibility with water; or
(ii) an ether solvent that has low miscibility with water and a coordinating co-solvent;
(c) treating the boronic ester compound of formula (XVI) with a reagent of formula $M^1$-N(G)$_2$, where $M^1$ is an alkali metal and each G individually or together is an amino group protecting group, to form a compound of formula (XVII):

(XVII)

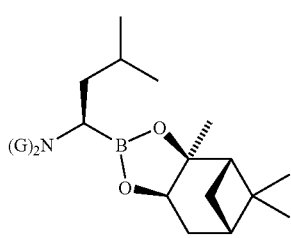

(d) removing the G groups to form a compound of formula (XVIII):

(XVIII)

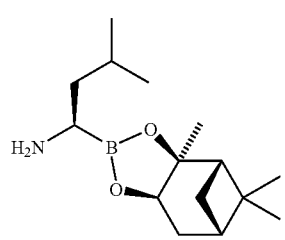

or an acid addition salt thereof;
(e) coupling the compound of formula (XVIII) with a compound of formula (XIX);

(XIX)

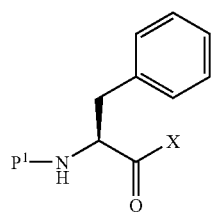

wherein:
$P^1$ is a cleavable amino group protecting moiety; and
X is OH or a leaving group;
to form a compound of formula (XX):

(XX)

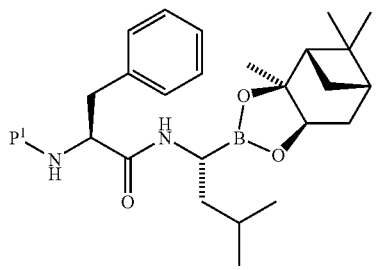

wherein $P^1$ is as defined above;
(f) removing the protecting group $P^1$ to form a compound of formula (XXI):

(XXI)

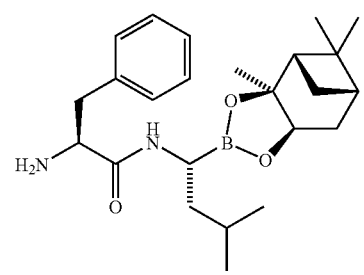

or an acid addition salt thereof;
(g) coupling the compound of formula (XXI) with a reagent of formula (XXII)

(XXII)

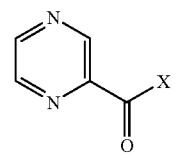

wherein X is a OH or a leaving group, to form a compound of formula (XXII):

(XXIII)

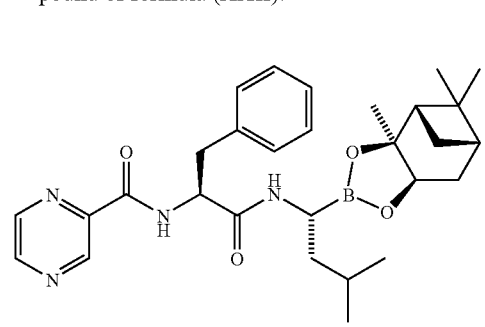

; and (h) deprotecting the boronic acid moiety to form the compound of formula (XIV) or a boronic acid anhydride thereof.

In some embodiments, the process is characterized by at least one of the following features (1)-(5). In certain preferred embodiments, the process is characterized by all five features (1)-(5) below.

(1) In the boron "ate" complex of formula (XV), $R^3$ and Y both are chloro.
(2) The coupling step (e) comprises the steps:

(i) coupling the compound of formula (XVIII) with a compound of formula (XIX) wherein X is OH in the presence of 2-(1H-benzotriazol-1-yl)-1,1,3,3-tetramethyluronium tetrafluoroborate (TBTU) and a tertiary amine in dichloromethane;

(ii) performing a solvent exchange to replace dichloromethane with ethyl acetate; and (iii) performing an aqueous wash of the ethyl acetate solution.

(3) The protecting group removing step (f) comprises the steps:

(i) treating the compound of formula (XX) with HCl in ethyl acetate;

(ii) adding heptane to the reaction mixture; and (iii) isolating by crystallization the compound of formula (XXI) as its HCl addition salt.

(4) The coupling step (g) comprises the steps:

(i) coupling the compound of formula (XXI) with 2-pyrazinecarboxylic acid in the presence of TBTU and a tertiary amine in dichloromethane;

(ii) performing a solvent exchange to replace dichloromethane with ethyl acetate; and (iii) performing an aqueous wash of the ethyl acetate solution.

(5) The boronic acid deprotecting step (h) comprises the steps:

(i) providing a biphasic mixture comprising the compound of formula (XXIII), an organic boronic acid acceptor, a lower alkanol, a $C_{5-8}$ hydrocarbon solvent, and aqueous mineral acid;

(ii) stirring the biphasic mixture to afford the compound of formula (XIV);

(iii) separating the solvent layers; and (iv) extracting the compound of formula (XIV), or a boronic acid anhydride thereof, into an organic solvent.

Preferably, step (h)(iii) comprises the steps:

(1) separating the solvent layers;

(2) adjusting the aqueous layer to basic pH;

(3) washing the aqueous layer with an organic solvent; and (4) adjusting the aqueous layer to a pH less than about 6;

In another embodiment, the invention relates to a large-scale process for forming a compound of formula (XIV)

(XIV)

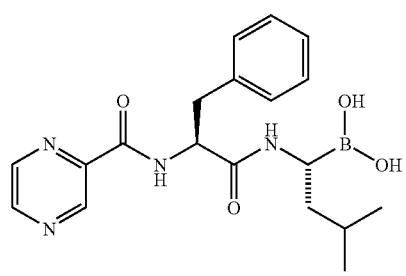

or a boronic acid anhydride thereof, comprising the steps:

(aa) coupling a compound of formula (XVIII):

(XVIII)

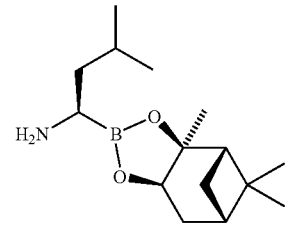

or an acid addition salt thereof, with a compound of formula (XIX):

(XIX)

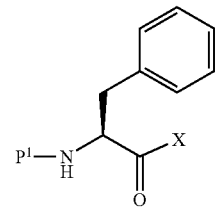

wherein:

$P^1$ is a cleavable amino group protecting moiety; and

X is OH or a leaving group;

to form a compound of formula (XX):

(XX)

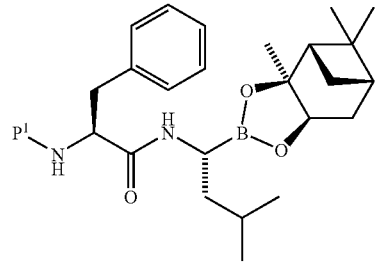

wherein $P^1$ is as defined above, said coupling step (aa) comprising the steps:

(i) coupling the compound of formula (XVIII) with a compound of formula (XIX) wherein X is OH in the presence of 2-(1H-benzotriazol-1-yl)-1,1,3,3-tetramethyluronium tetrafluoroborate (TBTU) and a tertiary amine in dichloromethane;

(ii) performing a solvent exchange to replace dichloromethane with ethyl acetate; and (iii) performing an aqueous wash of the ethyl acetate solution;

(bb) removing the protecting group $P^1$ to form a compound of formula (XXI):

(XXI)

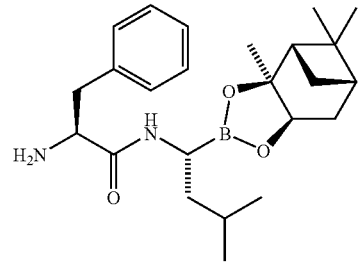

or an acid addition salt thereof, said protecting group removing step (bb) comprising the steps:
(i) treating the compound of formula (XX) with HCl in ethyl acetate;
(ii) adding heptane to the reaction mixture; and
(iii) isolating by crystallization the compound of formula (XXI) as its HCl addition salt;
(cc) coupling the compound of formula (XXI) with a reagent of formula (XXII)

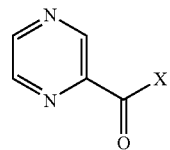

(XXII)

wherein X is a OH or a leaving group, to form a compound of formula (XXIII):

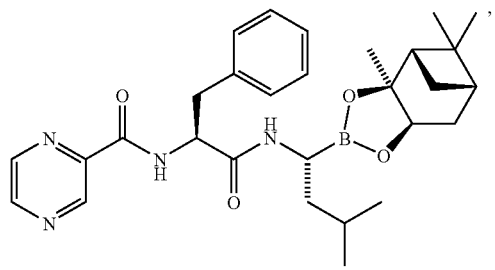

(XXIII)

said coupling step (cc) comprising the steps:
(i) coupling the compound of formula (XXI) with 2-pyrazinecarboxylic acid in the presence of TBTU and a tertiary amine in dichloromethane;
(ii) performing a solvent exchange to replace dichloromethane with ethyl acetate; and
(iii) performing an aqueous wash of the ethyl acetate solution; and
(dd) deprotecting the boronic acid moiety to form the compound of formula (XIV) or a boronic acid anhydride thereof, said deprotecting step (dd) comprising the steps:
(i) providing a biphasic mixture comprising the compound of formula (XXIII), an organic boronic acid acceptor, a lower alkanol, a $C_{5-8}$ hydrocarbon solvent, and aqueous mineral acid;
(ii) stirring the biphasic mixture to afford the compound of formula (XIV);
(iii) separating the solvent layers; and
(iv) extracting the compound of formula (XIV), or a boronic acid anhydride thereof, into an organic solvent.

Preferably, step (dd)(iii) comprises the steps:
(1) separating the solvent layers;
(2) adjusting the aqueous layer to basic pH;
(3) washing the aqueous layer with an organic solvent; and
(4) adjusting the aqueous layer to a pH less than about 6;

The efficiency of the processes described above is further enhanced by telescoping steps, for example, by carrying a reaction mixture or worked-up product solution from one reaction directly into the following reaction, without isolation of the intermediate product. For example, in some embodiments, step (e)(iii) or (aa)(iii) affords an ethyl acetate solution comprising a compound of formula (XX), and the ethyl acetate solution is directly subjected in step (f) or (bb) to conditions effective to remove the protecting group $P^1$. In some such embodiments, the protecting group $P^1$ is an acid-labile protecting group, for example, tert-butoxycarbonyl (Boc), and the ethyl acetate solution from step (e)(iii) or (aa)(iii) is treated with acid. In certain preferred embodiments, the ethyl acetate solution from step (e)(iii) or (aa)(iii) is dried azeotropically and then treated with gaseous HCl.

When the deprotecting step (f) or (bb) is performed under anhydrous conditions, as described above, the product of formula (XXI) can be isolated by crystallization from the reaction mixture as its HCl addition salt. Crystallization of the product salt is promoted by addition of a hydrocarbon solvent such as n-heptane. In some embodiments, the reaction mixture is partially concentrated prior to addition of the hydrocarbon solvent. The present inventors have discovered that crystallization of the compound of formula (XXI) in this manner efficiently removes any tripeptide impurity that may have formed during the coupling step (e) or (aa). Such impurities are difficult to remove at later stages in the synthesis.

Further telescoping of the process is possible by carrying the product mixture from the coupling step (g) or (cc) directly into the boronic acid moiety deprotecting step (h) or (dd). Preferably, the organic solvent from the coupling reaction is first replaced with ethyl acetate in order to facilitate aqueous washes. A second solvent exchange into a hydrocarbon solvent then permits the product solution from step (g) or (cc) to be used directly in the biphasic boronic acid deprotecting step (h) or (dd), without isolation of the compound of formula (XXIII).

Alternatively, a more convergent approach may be adopted for the synthesis of the compound of formula (XIV). Thus, in yet another embodiment, the invention provides a large-scale process for forming a compound of formula (XIV)

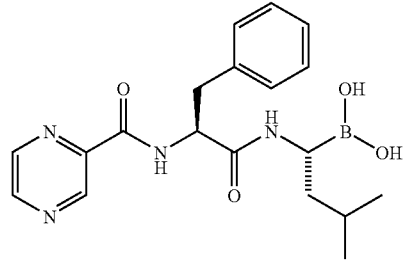

(XIV)

or a boronic acid anhydride thereof. The process comprises the steps:
(a) providing a boron "ate" complex of formula (XV):

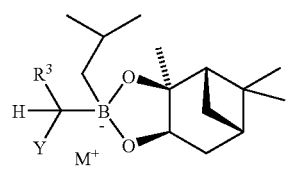

(XV)

wherein:
$R^3$ is a nucleofugic group;
Y is a nucleofugic group; and
$M^+$ is an alkali metal;
(b) contacting the boron "ate" complex of formula (XV) with a Lewis acid under conditions that afford a boronic ester compound of formula (XVI):

(XVI)

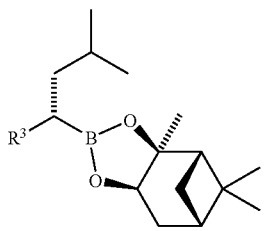

said contacting step being conducted in a reaction mixture comprising:
(i) a coordinating ether solvent that has low miscibility with water; or
(ii) an ether solvent that has low miscibility with water and a coordinating co-solvent;
(c) treating the boronic ester compound of formula (XVI) with a reagent of formula $M^1$-$N(Si(R^6)_3)_2$, where $M^1$ is an alkali metal and each $R^6$ independently is selected from the group consisting of alkyl, aralkyl, and aryl, where the aryl or aryl portion of the aralkyl is optionally substituted, to form a compound of formula (XVII):

(XVII)

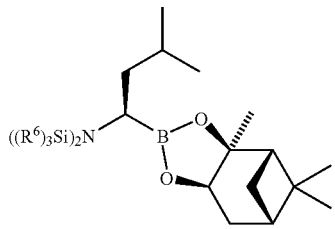

(d) removing the $(R^6)_3Si$ groups to form a compound of formula (XVIII):

(XVIII)

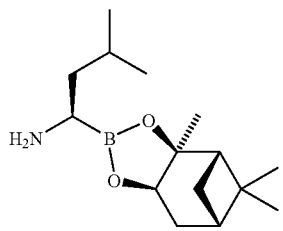

or an acid addition salt thereof;
(e') coupling the compound of formula (XVIII) with a compound of formula (XIXa):

(XIXa)

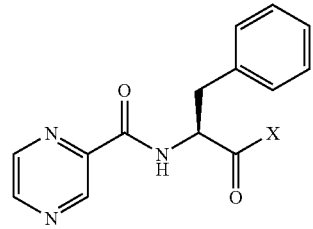

wherein X is OH or a leaving group, to form a compound of formula (XXIII):

(XXIII)

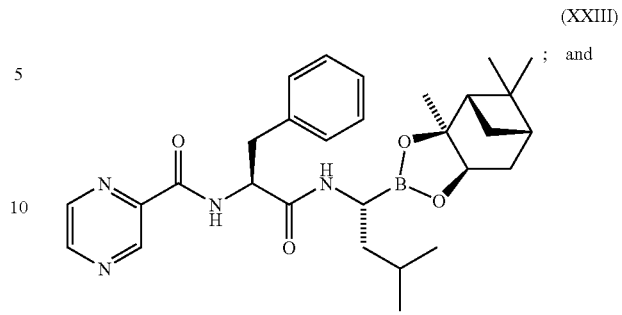

; and (f) deprotecting the boronic acid moiety to form the compound of formula (XIV) or a boronic acid anhydride thereof.

In some embodiments, the process is characterized by at least one of the following features (1)-(3). In certain preferred embodiments, the process is characterized by all three features (1)-(3) below.
(1) In the boron "ate" complex of formula (XV), $R^3$ and Y both are chloro.
(2) The coupling step (e') comprises the steps:
(i) coupling the compound of formula (XVIII) with a compound of formula (XIXa) wherein X is OH in the presence of 2-(1H-benzotriazol-1-yl)-1,1,3,3-tetramethyluronium tetrafluoroborate (TBTU) and a tertiary amine in dichloromethane;
(ii) performing a solvent exchange to replace dichloromethane with ethyl acetate; and
(iii) performing an aqueous wash of the ethyl acetate solution.
(3) The boronic acid deprotecting step (f) comprises the steps:
(i) providing a biphasic mixture comprising the compound of formula (XXIII), an organic boronic acid acceptor, a lower alkanol, a $C_{5-8}$ hydrocarbon solvent, and aqueous mineral acid;
(ii) stirring the biphasic mixture to afford the compound of formula (XIV);
(iii) separating the solvent layers; and
(iv) extracting the compound of formula (XIV), or a boronic acid anhydride thereof, into an organic solvent.

Preferably, step (f)(iii) comprises the steps:
(1) separating the solvent layers;
(2) adjusting the aqueous layer to basic pH;
(3) washing the aqueous layer with an organic solvent; and
(4) adjusting the aqueous layer to a pH less than about 6;

In step (h)(iv), (dd)(iv), or (f)(iv) of the processes described above, the compound of formula (XIV), or a boronic acid anhydride thereof, preferably is extracted into ethyl acetate and crystallized by addition of hexane or heptane. In some embodiments, the process further comprises isolation of a boronic acid anhydride of the compound of formula (XIV), preferably a trimeric boronic acid anhydride of formula (XXIV):

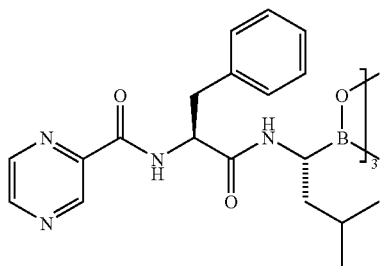

(XXIV)

The processes of the invention permit the large-scale manufacture of bortezomib of very high chemical and stereochemical purity. Prior art processes were limited in scale and afforded product of lower overall purity. In yet another aspect, therefore, the invention provides a composition comprising at least one kilogram of a compound of formula (XXIV):

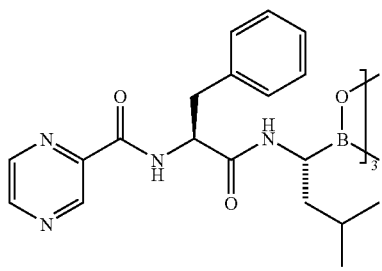

(XXIV)

The compound of formula (XXIV) preferably is prepared according to the process described above, and preferably constitutes at least 99% w/w of the composition according to this aspect of the invention.

EXAMPLES

| Abbreviations | |
|---|---|
| BOC | tert-butoxycarbonyl |
| D.I. | de-ionized |
| DMF | N,N-dimethylformamide |
| GC | gas chromatography |
| GC-MS | gas chromatography-mass spectrometry |
| h | hours |
| HDPE | high density polyethylene |
| HPLC | high performance liquid chromatography |
| LDA | lithium diisopropylamide |
| LOD | loss on drying |
| min | minutes |
| MTBE | t-butyl methyl ether |
| RP-HPLC | reverse phase high performance liquid chromatography |
| RPM | revolutions per minute |
| TBTU | O-benzotriazol-1-yl-N,N,N',N'-tetramethyluronium tetrafluoroborate |
| THF | tetrahydrofuran |

Example 1

(1R)-(S)-Pinanediol 1-ammonium trifluoroacetate-3-methylbutane-1-boronate Manufacturing Process (1S)-(S)-Pinanediol 1-chloro-3-methylbutane-1-boronate 1. (S)-Pinanediol-2-methylpropane-1-boronate (12.0 kg, 50.8 moles) was charged to a reaction vessel maintained under a nitrogen atmosphere.

2. tert-Butyl methyl ether (53 kg) and dichloromethane (22.5 kg) were charged and the resultant mixture was cooled to −57° C. with stirring.

3. Diisopropylamine, (6.7 kg) was charged to another reaction vessel maintained under a nitrogen atmosphere.

4. tert-Butyl methyl ether (27 kg) was charged to the diisopropylamine and the resultant mixture was cooled to −10° C. with stirring.

5. n-Hexyllithium in hexane (33.2 weight % solution) (17.6 kg) was added to the diisopropylamine mixture over a period of 57 minutes, while the reaction temperature was maintained at −10° C. to −7° C.

6. This mixture (LDA-mixture) was stirred for 33 minutes at −9° C. to −7° C. before it was used.

7. Zinc chloride, (12.1 kg) was charged to a third reaction vessel maintained under a nitrogen atmosphere.

8. tert-Butyl methyl ether (16 kg) was charged to the zinc chloride and the resultant mixture was warmed to 30° C. with stirring.

9. Tetrahydrofuran (53 kg) was added to the zinc chloride suspension over a period of 18 minutes, while the reaction temperature was maintained at 35° C. to 40° C.

10. This mixture ($ZnCl_2$-mixture) was stirred for 4 hours and 28 minutes at 38° C. to 39° C. until it was used.

11. The LDA-mixture (from # 3-6) was added over a period of 60 minutes to the reaction vessel containing (S)-pinanediol-2-methylpropane-1-boronate, while the reaction temperature was maintained at −60° C. to −55° C.

12. A tert-butyl methyl ether rinse (10 kg) was used to complete the addition.

13. The reaction mixture was stirred for an additional 20 minutes at −59° C. to −55° C.

14. The reaction mixture was warmed to −50° C. over a period of 11 minutes.

15. The $ZnCl_2$-mixture (from # 7-10) was added over a period of 48 minutes to the reaction vessel containing (S)-pinanediol-2-methylpropane-1-boronate and the LDA-mixture, while the reaction temperature was maintained at −50° C. to −45° C.

16. A tert-butyl methyl ether rinse (10 kg) was used to complete the addition.

17. The reaction mixture was stirred for an additional 30 minutes at −45° C. to −40° C. and then warmed to 10° C. over a period of 81 minutes.

18. A 10% sulfuric acid solution (72 kg) was added over a period of 40 minutes to the reaction vessel, while the reaction temperature was maintained at 10° C. to 21° C.

19. The reaction mixture was stirred for 16 minutes at ambient temperature, before the aqueous phase was separated.

20. The organic phase was washed successively with deionized (D.I.) water (32 kg), and 10% sodium chloride solution (26.7 kg), each wash involved vigorous stirring for 15 to 17 minutes at ambient temperature.

21. The reaction mixture was concentrated under reduced pressure ($p_{min}$=81 mbar), maintaining an external (jacket/bath) temperature of 50° C. to 55° C., providing a residue which was dissolved in methylcyclohexane (56 kg).

22. The reaction mixture was refluxed (in a Dean-Stark type condenser for water separation) under reduced pressure ($p_{min}$=67 mbar), maintaining an external (jacket/bath) temperature of 50° C. to 55° C. for 2 hours and 7 minutes, until no more water was separated.

23. About 35 L of the solvents were distilled off under reduced pressure ($p_{min}$=81 mbar), maintaining an external (jacket/bath) temperature of 50° C. to 55° C.

24. The resultant dry methylcyclohexane mixture containing (1S)-(S)-pinanediol 1-chloro-3-methylbutane-1-boronate was cooled to 14° C.

(1R)-(S)-Pinanediol 1-bis(trimethylsilyl)amino-3-methylbutane-1-boronate

1. Lithium bis(trimethylsilyl)amide in tetrahydrofuran (19.4 weight % solution), (41.8 kg) was charged to a reaction vessel maintained under a nitrogen atmosphere and cooled to −19° C. with stirring.
2. The methylcyclohexane mixture containing (1S)-(S)-pinanediol 1-chloro-3-methylbutane-1-boronate was added over a period of 55 minutes, while the reaction temperature was maintained at −19° C. to −13° C.
3. A methylcyclohexane rinse (5 kg) was used to complete the addition.
4. The reaction mixture was stirred for an additional 65 minutes at −13° C. to −12° C. and then warmed to 25° C. over a period of 25 minutes.
5. A suspension of Celite (2.5 kg) in methylcyclohexane (22 kg) was added to the reaction mixture.
6. The reaction mixture was concentrated under reduced pressure ($p_{min}$=25 mbar), maintaining an external (jacket/bath) temperature of 45° C. to 50° C., providing a residue which was dissolved in methylcyclohexane (36 kg).
7. A sample was then removed for in-process testing for tetrahydrofuran content by GC.
8. The tetrahydrofuran assay was 0.58%.
9. The solids were removed by filtration, the filtrate was filtered through a plug of Silica Gel (2.0 kg).
10. Both filter units were washed with isopropyl ether (30 kg).
11. The resultant methylcyclohexane/isopropyl ether mixture containing (1R)-(S)-pinanediol 1-bis(trimethylsilyl)amino-3-methylbutane-1-boronate was stored in a container at ambient temperature until it was used in the next step.

(1R)-(S)-Pinanediol 1-ammonium trifluoroacetate-3-methylbutane-1-boronate

1. Trifluoroacetic acid, (12 kg) was charged to another reaction vessel maintained under a nitrogen atmosphere.
2. Isopropyl ether (78 kg) was charged to the trifluoroacetic acid and the resultant mixture was cooled to −10° C. with stirring.
3. The methylcyclohexane/isopropyl ether mixture containing (1R)-(S)-pinanediol 1-bis(trimethylsilyl)amino-3-methylbutane-1-boronate was added over a period of 53 minutes causing product precipitation, while the reaction temperature was maintained at −10° C. to −5° C.
4. An isopropyl ether rinse (5 kg) was used to complete the addition.
5. The reaction mixture was stirred for an additional 8 hours and 20 minutes at −9° C. to −7° C.
6. The solid was collected by filtration, washed with isopropyl ether (70 kg) in two portions, and dried under reduced pressure (pmin=56 mbar) at 41° C. to 42° C. for 2 hours and 15 minutes.
7. The solid was stirred with D.I. water (60 kg) for 24 minutes at ambient temperature, before the D.I. water was removed by filtration.
8. The solid was washed with D.I. water (12 kg).
9. The solid was then dried under vacuum (pmin=4 mbar) at 40° C. to 44° C. for 9 hours and 22 minutes, after that time the loss on drying was 0.51%, which meets the ≦1% requirement.
10. The intermediate, (1R)-(S)-pinanediol 1-ammonium trifluoroacetate-3-methylbutane-1-boronate, crude, was then packaged into single polyethylene bags in polypropylene drums and labeled. The yield was 72%.

Recrystallization of (1R)-(S)-pinanediol 1-ammonium trifluoroacetate-3-methylbutane-1-boronate, crude 1. (1R)-(S)-Pinanediol 1-ammonium trifluoroacetate-3-methylbutane-1-boronate, crude, (13 kg) was charged to a reaction vessel maintained under a nitrogen atmosphere.
2. Trifluoroacetic acid (31 kg) was charged to the reaction vessel and the resultant mixture was cooled to 4° C. with stirring.
3. Once all of the solid was dissolved leaving a slightly turbid mixture, isopropyl ether (29 kg) was added over a period of 57 minutes, while the reaction temperature was maintained at 2° C. to 3° C.
4. After complete addition the mixture was filtered through a filter into a receiving vessel maintained under a nitrogen atmosphere.
5. Reactor and filter were rinsed with a mixture of trifluoroacetic acid (3.8 kg) and isopropyl ether (5 kg). The rinse was added to the filtrate.
6. Isopropyl ether (126 kg) was added over a period of 15 minutes causing product precipitation, while the reaction temperature was maintained at 16° C. to 18° C.
7. The mixture was stirred at 16° C. to 18° C. for 15 min, then cooled to −5° C. over a period of 67 minutes, and stirred at −3° C. to −5° C. under a nitrogen atmosphere for 89 minutes.
8. The solid was then isolated by filtration, washed with isopropyl ether (48 kg) in two portions, and dried under vacuum (pmin=2 mbar) at 34° C. to 40° C. for 2 hours and 55 minutes after that time the loss on drying was 0.32%, which meets the ≦0.5% requirement.
9. The product, (1R)-(S)-pinanediol 1-ammonium trifluoroacetate-3-methylbutane-1-boronate, was then packaged into double polyethylene bags in fiber drums and labeled. The yield was 86%.

Example 2

N-(2-Pyrazinecarbonyl)-L-phenylalanine-L-leucine boronic anhydride Manufacturing Process

(1S,2S,3R,5S)-Pinanediol N-BOC-L-phenylalanine-L-leucine boronate

1. In a fume hood, a three-necked glass reaction flask equipped with a Claisen head temperature recorder and a mechanical stirrer was flushed with nitrogen.
2. (1R)-(S)-Pinanediol 1-ammonium trifluoroacetate-3-methylbutane-1-boronate (2.0 kg), was charged to the flask.
3. BOC-L-phenylalanine (1.398 kg) was charged to the flask.
4. 2-(1H-Benzotriazol-1-yl)-1,1,3,3-tetramethyl uronium tetrafluoroborate, TBTU (1.864 kg) was charged to the flask.
5. Dichloromethane (15.8 L) was charged to the flask.
6. The stirring motor was adjusted to provide stirring at 260 RPM.
7. Using an ice/water cooling bath, the reaction mixture was cooled to 1.0° C., maintaining a nitrogen atmosphere.
8. N,N-Diisopropylethylamine (2.778 L) was charged to a glass flask and transferred to the reaction mixture over a period of 117 minutes using a peristaltic pump maintaining a reaction temperature range of 0.7° C.-2.1° C. The overall addition rate was 23.7 mL/min.

9. A dichloromethane (0.2 L) rinse of the flask into the reaction mixture was used to complete the addition.

10. The reaction mixture was stirred for an additional 35 minutes. The temperature at the start of the stir time was 1.8° C., and 2.5° C. at the end.

11. A sample was then removed for in-process testing by reverse phase high performance liquid chromatography (RP-HPLC). The percent conversion was determined to be 99.3%.

12. The reaction mixture was transferred in approximately two equal halves to two rotary evaporator flasks. The reaction mixture was concentrated under reduced pressure using a rotary evaporator, maintaining an external bath temperature of 29-30° C.

13. Ethyl acetate (4.0 L) was divided into two approximately equal portions and charged to the two rotary evaporator flasks.

14. The mixtures in each flask were again concentrated under reduced pressure using a rotary evaporator, maintaining an external bath temperature of 29-30° C.

15. The residues in each rotary evaporator flask were then transferred back to the reaction flask using ethyl acetate (13.34 L).

16. In a glass flask equipped with a stirrer, a 1% aqueous phosphoric acid solution was prepared by mixing D.I. water (13.18 L) and phosphoric acid (0.160 kg).

17. In a glass flask equipped with a stirrer, a 2% aqueous potassium carbonate solution (12.0 L) was prepared by mixing D.I. water (11.76 L) and potassium carbonate (0.24 kg).

18. In a glass flask equipped with a stirrer, a 10% aqueous sodium chloride solution (13.34 L) was prepared by mixing D.I. water (13.34 L) and sodium chloride (1.334 kg).

19. D.I. water (13.34 L) was charged to the reaction flask containing the ethyl acetate solution and the mixture stirred at 380 RPM for 7 minutes. The layers were allowed to separate and the aqueous phase (bottom layer) was transferred under vacuum to a suitable flask and discarded.

20. Again, D.I. water (13.34 L) was charged to the reaction flask containing the ethyl acetate solution and the mixture stirred at 385 RPM for 7 minutes. The layers were allowed to separate and the aqueous phase (bottom layer) was transferred under vacuum to a suitable flask and discarded.

21. The 1% phosphoric acid solution prepared in Step 16 was charged to the reaction flask containing the ethyl acetate solution and the mixture stirred at 365 RPM for 7 minutes. The layers were allowed to separate and the acidic aqueous phase (bottom layer) was transferred to a suitable flask and discarded.

22. The 2% potassium carbonate solution prepared in Step 17 was charged to the reaction flask containing the ethyl acetate solution and the mixture stirred at 367 RPM for 7 minutes. The layers were allowed to separate and the basic aqueous phase (bottom layer) was transferred to a suitable flask and discarded.

23. The 10% sodium chloride solution prepared in Step 18 was charged to the reaction flask containing the ethyl acetate solution and the mixture stirred at 373 RPM for 6 minutes. The layers were allowed to separate and the aqueous phase (bottom layer) was transferred to a suitable flask and discarded.

24. The ethyl acetate solution was transferred to a rotary evaporator flask and concentrated under reduced pressure using a rotary evaporator, maintaining a bath temperature of 29-30° C., to provide a residue.

25. The residue was then redissolved in ethyl acetate (4.68 L).

26. The solution was concentrated under vacuum using a rotary evaporator, maintaining a bath temperature of 29-30° C., to provide a residue once more.

27. Again, the residue was then redissolved in ethyl acetate (4.68 L) and two samples taken for determination of water content by Karl Fisher titration. The water content of two samples was determined as 0.216% and 0.207%.

28. Using a further quantity of ethyl acetate (12.66 L), the mixture was transferred from the rotary evaporator flask to a dry reaction flask equipped with a temperature recorder, a mechanical stirrer, and a fritted gas dispersion tube, and purged with nitrogen.

(1S,2S,3R,5S)-Pinanediol L-phenylalanine-L-leucine boronate, HCl salt

1. The ethyl acetate solution containing (1S,2S,3R,5S)-pinanediol N-BOC-L-phenylalanine-L-leucine boronate was cooled using an ice/water cooling bath to −0.9° C.

2. Hydrogen chloride (1.115 kg) gas was bubbled into the reaction mixture over a period of 1.48 hours. The temperature at the start of the addition was −0.9° C., and 6.8° C. at the end.

3. The reaction was then allowed to warm to 14.4° C. over 50 minutes, while maintaining a nitrogen atmosphere.

4. A sample was removed for in-process testing by RP-HPLC. The percent conversion was 68.9% (area %).

5. The reaction was stirred for 35 minutes. The temperature at the start was 14° C., and 14.8° C. at the end.

6. A sample was removed for in-process testing by RP-HPLC. The percent conversion was 94.7% (area %).

7. The reaction was stirred for approximately a further 50 minutes, maintaining a temperature of 10° C.±5° C.

8. A sample was removed for in-process testing by RP-HPLC. The percent conversion was 97.3%.

9. The reaction was stirred for approximately a further 50 minutes, maintaining a temperature of 10° C.±5° C. The final temperature was 14.6° C.

10. A sample was removed for in-process testing by RP-HPLC. The total reaction time after addition of hydrogen chloride gas was four (4) hours.

11. The percent conversion was 99%.

12. A slurry was observed.

13. n-Heptane (8.8 L) was charged to the reaction mixture.

14. The slurry was stirred for 2 hours. The temperature at the start of the stir time was 12.7° C., and 15.3° C. at the end.

15. The solid was isolated by filtration on a Buchner funnel lined with a polypropylene felt filter pad.

16. The solid was washed with n-heptane (4.68 L).

17. In a hood, the solid was transferred to three drying trays at not more than 1" deep and air-dried for 1 hour.

18. The solid was then dried at ≦35° C. under a vacuum of 27" of Hg for 16 hours 28 minutes in a vacuum oven equipped with a vacuum gauge and a temperature recorder.

19. The solid was sampled from each drying tray to determine the % Loss on Drying. The LOD was determined to be 0%, 0.02%, and 0.02% on the three samples taken.

20. (1S,2S,3R,5S)-Pinanediol L-phenylalanine-L-leucine boronate, HCl salt was then packaged into double poly bags in fiber drums and labeled, and sampled.

21. The isolated yield was 1.87 kg, 79.1%. The intermediate was stored at 2-8° C. until used in further manufacturing.

(1S,2S,3R,5S)-Pinanediol N-(2-pyrazinecarbonyl)-L-phenylalanine-L-leucine boronate 1. In a fume hood a three-necked glass reaction flask equipped with a Claisen head, temperature recorder and a mechanical stirrer was flushed with nitrogen.
2. (1S,2S,3R,5S)-Pinanediol L-phenylalanine-L-leucine boronate, HCl salt (1.85 kg) was charged to the flask.
3. 2-Pyrazinecarboxylic acid (0.564 kg) was charged to the flask.
4. 2-(H-Benzotriazol-1-yl)-1,1,3,3-tetramethyl uronium tetrafluoroborate, TBTU (1.460 kg) was charged to the flask.
5. Dichloromethane (18.13 L) was charged to the flask.
6. The stirring motor was adjusted to provide stirring at 272 RPM.
7. Using a cooling bath, the reaction mixture was cooled to −1.2° C.
8. N,N-Diisopropylethylamine (1.865 kg) was charged to a glass flask and transferred to the reaction over a period of 50 minutes using a peristaltic pump maintaining a reaction temperature range of −1.2° C. to 2.8° C.
9. A dichloromethane rinse (0.37 L) of the flask into the reaction mixture was used to complete the addition.
10. The reaction mixture was allowed to warm and stirred for an additional 81 minutes.
11. The temperature at the start of the stir time was 15° C., and 24.9° C. at the end.
12. A sample was then removed for in-process testing by RP-HPLC. The percent conversion was determined to be 99.9%.
13. The reaction mixture was transferred in approximately two equal halves to two rotary evaporator flasks. The reaction mixture was concentrated under reduced pressure using two rotary evaporators, maintaining an external bath temperature of 33-34° C.
14. Ethyl acetate (12.95 L) was divided into two approximately equal portions and charged to the two rotary evaporator flasks.
15. The mixtures in each flask were then concentrated under reduced pressure using a rotary evaporator, maintaining an external bath temperature of 33-34° C.
16. The residues in each rotary evaporator flask were then transferred back to the reaction flask using ethyl acetate (12.95 L).
17. In a glass flask equipped with a stirrer, a 1% aqueous phosphoric acid solution (12.34 L) was prepared by mixing D.I. water (12.19 L) and phosphoric acid (0.148 kg).
18. In a glass flask equipped with a stirrer, a 2% aqueous potassium carbonate solution (12.34 L) was prepared by mixing D.I. water (12.09 L) and potassium carbonate (0.247 kg).
19. In a glass flask equipped with a stirrer, a 10% aqueous sodium chloride solution (12.34 L) was prepared by mixing D.I. water (12.34 L) and sodium chloride (1.234 kg).
20. D.I. water (12.34 L) was charged to the reaction flask containing the ethyl acetate solution and the mixture stirred at 382 RPM for 7 minutes. The layers were allowed to separate and the aqueous phase (bottom layer) was transferred to a suitable flask and discarded.
21. Again, D.I. water (12.34 L) was charged to the reaction flask containing the ethyl acetate solution and the mixture stirred at 398 RPM for 7 minutes. The layers were allowed to separate and the aqueous phase (bottom layer) was transferred to a suitable flask and discarded.
22. The 1% phosphoric acid solution prepared in Step 17 was charged to the reaction flask containing the ethyl acetate solution and the mixture stirred at 364 RPM for 8 minutes. The layers were allowed to separate and the acidic aqueous phase (bottom layer) was transferred to a suitable flask and discarded.
23. The 2% potassium carbonate solution prepared in Step 18 was charged to the reaction flask containing the ethyl acetate solution and the mixture stirred at 367 RPM for 8 minutes. The layers were allowed to separate and the basic aqueous phase (bottom layer) was transferred to a suitable flask and discarded.
24. The 10% sodium chloride solution prepared in Step 19 was charged to the reaction flask containing the ethyl acetate solution and the mixture stirred at 374 RPM for 8 minutes. The layers were allowed to separate and the aqueous phase (bottom layer) was transferred to a suitable flask and discarded.
25. The ethyl acetate solution was transferred under vacuum in approximately two equal halves to two rotary evaporator flasks and concentrated under reduced pressure using a rotary evaporator, maintaining an external bath temperature of 34° C.
26. n-Heptane (14.8 L) was divided into two approximately equal portions and charged to the two rotary evaporator flasks. The mixtures in each flask were then concentrated under reduced pressure using a rotary evaporator, maintaining an external bath temperature of 34° C.

N-(2-Pyrazinecarbonyl)-L-phenylalanine-L-leucine boronic anhydride, crude

1. In a glass flask equipped with a stirrer, a 1N solution of hydrochloric acid (22.2 L) was prepared by mixing D.I. water (20.36 L) and hydrochloric acid (1.84 kg).
2. In a glass flask equipped with a stirrer, a 2N sodium hydroxide solution (12.03 L) was prepared by mixing D.I. water (12.03 L) and sodium hydroxide (0.962 kg).
3. The residues containing (1S,2S,3R,5S)-pinanediol N-(2-pyrazinecarbonyl)-L-phenylalanine-L-leucine boronate in each rotary evaporator flask were then transferred to a three-necked glass reaction flask equipped with a temperature recorder and a mechanical stirrer, using n-heptane (14.8 L) and methanol (14.8 L).
4. The stirring motor was adjusted to provide stirring at 284 RPM.
5. 2-Methylpropaneboronic acid (0.672 kg) was charged to the flask.
6. 1N hydrochloric acid prepared in Step 1 (11.2 L) was charged to the flask.
7. The stirring motor was adjusted to provide stirring at 326 RPM.
8. The reaction mixture was stirred for 16.38 hours The start batch temperature was 28.6° C., and the end batch temperature was 21.6° C.
9. A sample was then removed for in-process testing by RP-HPLC.
10. The percent conversion was determined to be 100%.
11. Stirring was stopped and the biphasic mixture allowed to separate.
12. The n-heptane layer (upper layer) was transferred to a suitable flask and discarded.
13. n-Heptane (5.37 L) was charged to the reaction flask and the mixture stirred at 381 RPM for 6 minutes. The layers were allowed to separate and the n-heptane phase (upper layer) was transferred to a suitable flask and discarded.
14. Again, n-heptane (5.37 L) was charged to the reaction flask and the mixture stirred at 340 RPM for 6 minutes. The layers were allowed to separate and the n-heptane phase (upper layer) was transferred to a suitable flask and discarded.

15. The aqueous methanol solution was transferred in approximately two equal halves to two rotary evaporator flasks and concentrated under reduced pressure using a rotary evaporator, maintaining an external bath temperature of 33-34° C. 15 L of methanol were collected.

16. Dichloromethane (5.37 L) was used to transfer the residue from the rotary evaporator flasks back into the reaction flask.

17. 2N sodium hydroxide (11.2 L) prepared in Step 2 was charged to the flask.

18. The dichloromethane layer (lower layer) was transferred to a suitable flask and discarded.

19. Dichloromethane (5.37 L) was charged to the flask and the mixture stirred at 374 RPM for 6 minutes. The phases were allowed to separate and the dichloromethane layer (lower layer) was transferred to a suitable flask and discarded.

20. Again, dichloromethane, (5.37 L) was charged to the flask and the mixture stirred at 368 RPM for 8 minutes. The phases were allowed to separate and the dichloromethane layer (lower layer) was transferred to a suitable flask and discarded.

21. Dichloromethane (5.37 L) was charged to the flask.

22. 1N hydrochloric acid (10.7 L) was charged to the flask with stirring. The pH of the aqueous phase was determined to be 6.

23. Stirring was discontinued and the phases allowed to separate.

24. The dichloromethane phase (lower layer) was transferred under vacuum to a glass receiving flask.

25. Dichloromethane (5.37 L) was charged to the flask and the mixture stirred at 330 RPM for 6 minutes. The phases were allowed to separate and the dichloromethane layer (lower layer) was transferred to the glass receiving flask.

26. Again, dichloromethane, (5.37 L) was charged to the flask and the mixture stirred at 335 RPM for 6 minutes. The phases were allowed to separate and the dichloromethane layer (lower layer) was transferred to the glass receiving flask.

27. The dichloromethane extracts were combined and transferred in approximately two equal halves to two rotary evaporator flasks and concentrated under reduced pressure using a rotary evaporator, maintaining an external bath temperature of 33-34° C.

28. Ethyl acetate (12.95 L) was divided into two approximately equal portions and charged to the two rotary evaporator flasks. The mixtures in each flask were then concentrated under reduced pressure using a rotary evaporator, maintaining an external bath temperature of 45-46° C.

29. Again, ethyl acetate (12.95 L) was divided into two approximately equal portions and charged to the two rotary evaporator flasks. The mixtures in each flask were then concentrated under reduced pressure using a rotary evaporator, maintaining an external bath temperature of 45-46° C., until approximately 10% of the original volume remained.

30. n-Heptane (10.2 L) was divided into two approximately equal portions and charged to the two rotary evaporator flasks, and the slurry stirred under a nitrogen atmosphere for 2.67 hours at 22-23° C.

31. The solid was isolated by filtration on a Buchner funnel, lined with a polypropylene felt filter pad.

32. The solid was washed with n-heptane (2.96 L).

33. In a hood, the solid was transferred to four drying trays and air-dried for 1.25 hours.

34. The solid was then dried at 36-50° C. under a vacuum of 27" of Hg for 18 hours 27 minutes in a vacuum oven equipped with a vacuum gauge and a temperature recorder.

35. The solid was sampled from each tray to determine the % Loss on Drying (LOD). The LOD was determined to be 0.38%, 0.62%, 0.71%, and 0.63% on the four samples taken.

36. N-(2-Pyrazinecarbonyl)-L-phenylalanine-L-leucine boronic anhydride, crude was packaged into two 5 L, HDPE, tamper-proof wide-mouth bottles and labeled.

37. The isolated yield was 1.314 kg, 83%.

Recrystallization of
N-(2-Pyrazinecarbonyl)-L-phenylalanine-L-leucine
boronic anhydride, crude 1. In a hood a glass reaction flask equipped with a mechanical stirrer, a reflux condenser and a temperature recorder was flushed with nitrogen.

2. Ethyl acetate (21 L) was charged to the flask.

3. The ethyl acetate was heated to 66.8° C. under a nitrogen atmosphere, using a hot water/steam bath.

4. N-(2-Pyrazinecarbonyl)-L-phenylalanine-L-leucine boronic anhydride, crude (1.311 kg) was slowly charged to the reaction flask. Charging occurred over a period of 3 minutes.

5. The mixture was stirred for 1 minute until all the solid had dissolved. The temperature of the solution was 64° C.

6. The heat source was removed and the mixture was slowly cooled to 60° C. using a cold bath.

7. The hot ethyl acetate solution was transferred into a receiving flask via poly tubing and a polypropylene in-line filter capsule using a peristaltic pump.

8. The mixture was allowed to cool to 27.2° C., and allowed to stand under a nitrogen atmosphere without stirring, for 17.75 hours. The final temperature was recorded as 20.5° C.

9. The mixture was cooled using an ice/water bath with stirring for 2.33 hours. The temperature at the start of the stir time was 3.8° C., and −2.8° C. at the end.

10. The solid was isolated by filtration on a Buchner funnel lined with a polypropylene felt filter pad. The filtrate was collected in a collection flask.

11. The solid was washed with ethyl acetate (2.62 L), cooled to 4.7° C.

12. In a hood, the solid was transferred to two drying trays.

13. The solid was then dried at 51-65° C. under a vacuum of 27" of Hg for 19 hours 10 minutes in a vacuum oven equipped with a vacuum gauge and a temperature recorder.

14. The solid was sampled to determine the % Loss on Drying (LOD). The LOD was determined to be 0.65% and 0.62% on the two samples taken.

15. N-(2-Pyrazinecarbonyl)-L-phenylalanine-L-leucine boronic anhydride was packaged into four 1 L, Type 3, Amber Wide-Mouth Bottles with Teflon-Lined Caps and labeled.

16. The isolated yield was 1.132 kg, 86.3%.

17. N-(2-Pyrazinecarbonyl)-L-phenylalanine-L-leucine boronic anhydride was stored at −25 to −15° C.

Example 3

N-(2-Pyrazinecarbonyl)-L-phenylalanine-L-leucine
boronic anhydride Convergent Synthesis (1S,2S,3R,5S)-Pinanediol N-(2-pyrazinecarbonyl)-
L-phenylalanine-L-leucine boronate A solution of (1R)-(S)-Pinanediol 1-ammonium trifluoroacetate-3-methylbutane-1-boronate (13.97 g) and N-hydroxysuccinimide (6.23 g) of in 66 mL of DMF was cooled to −5° C., followed by the addition of dicyclohexylcarbodiimide (10.83 g). The resulting suspension was stirred for one hour at a temperature of −5 to 0° C. To a solution of N-(2-pyrazinecarbonyl)-L-phenylalanine (19.52 g; prepared by coupling the preformed succinimide ester of pyrazinecarboxylic acid with L-phenylalanine in dioxane-water) in 62 mL of DMF was added N-methylmorpholine (5.7 mL) at a temperature of 0° C., and the resulting solution was added to the suspension. The suspension was adjusted to pH 7 by the addition of another 5.7 mL of N-methylmorpholine and stirred overnight, raising the temperature slowly to 21° C. After filtration, the filtercake was washed twice with MTBE and the combined filtrates were diluted with 950 mL of MTBE. The organic layer was washed with 20% aqueous citric acid (3×150 mL), 20% aqueous NaHCO₃ (3×150 mL), and brine (2×). The organic layer was dried over Na₂SO₄, filtered, and concentrated, yielding 25.5 g (95.5%) of the title compound as a foam. As indicated by tlc this material contained some minor impurities, including approximately 2% of cyclohexyl urea.

N-(2-Pyrazinecarbonyl)-L-phenylalanine-L-leucine boronic anhydride

A solution of (1S,2S,3R,5S)-Pinanediol N-(2-pyrazinecarbonyl)-L-phenylalanine-L-leucine boronate (25.2 g) in 207 mL of MeOH and 190 mL of hexane was cooled to 15° C., and 109.4 mL of 1N HCl were added in portions, keeping the temperature between 15 and 25° C. 2-Methylpropaneboronic acid (8.67 g) was then added under vigorous stirring, and the stirring of the biphasic mixture was continued over night. After separation of the two phases, the lower layer was extracted once with 75 mL of hexane. The lower layer was then concentrated in vacuo until it became cloudy, followed by the addition of 109.4 mL of 2N NaOH and 100 mL of Et₂O. The two phases were separated the lower layer was extracted with Et₂O (4×100 mL each), and then brought to pH 6.0 by the addition of 109 mL of 1N HCl. After extraction with 100 mL of ethyl acetate, the lower layer was adjusted to pH 6.0 with 1N HCl and extracted one more time with 75 mL of ethyl acetate. The combined ethyl acetate layers were washed with semi-saturated brine (2×25 mL) and brine (2×25 mL), dried over Na₂SO₄, filtered, and concentrated to afford 15.3 g (81.8%) of crude N-(2-Pyrazinecarbonyl)-L-phenylalanine-L-leucine boronic anhydride as a foam. The crude material was dissolved in 150 mL of ethyl acetate and concentrated in vacuo to a suspension, followed by the addition of 150 mL of MTBE. The suspension was stored between 2 and 8° C. over night, filtered, washed twice with MTBE, and dried under high vacuum, yielding 10.69 g (57.2%) of N-(2-pyrazinecarbonyl)-L-phenylalanine-L-leucine boronic anhydride as a white solid.

Example 4

Measurement of Diastereomeric Ratio of (1R)-(1S,2S,3R,5S)-Pinanediol-1-ammoniumtrifluoroacetate-3-methylbutane-1-boronate The diastereomeric purity of (1R)-(1S,2S,3R,5S)-pinanediol-1-ammoniumtrifluoroacetate-3-methylbutane-1-boronate (compound 1) was determined by non-chiral gas chromatography (GC).

| Chemicals: | Acetonitrile (p.a. Bruker or equivalent) |
| --- | --- |
| | Tetradecane (internal standard) (Fluka puriss. or equivalent) |
| | Trifluoroacetic anhydride (TFAA) (p.a. Merck or equivalent) |
| Instrument: | Trace-GC 2000 system or equivalent |
| Mobile phase: | H₂ |
| Solvent A (with internal standard) | Approximately 300 mg of tetradecane were weighed with an accuracy of 0.1 mg into a 100-mL volumetric flask. 1.5 mL of TFAA were added and the flask was brought to volume with acetonitrile. |
| Sample Preparation: | About 150 mg of the sample were exactly weighed (within 0.1 mg) into a 10-mL volumetric flask. The flask was brought to volume with Solvent A. The solution was stored for 15 minutes before injection. |
| GC Parameters: | |
| Column: | Rtx-200; 105 m × 0.25 mm i.d. × 0.25 µm film |
| Mobile phase: | H₂ |
| Temp. program: | 130° C. (0.5 min); 0.5° C./min to 200° C. (0 min); 30° C./min to 300 ° C. (2 min) |
| Flow: | 0.9 mL/min (const. flow) |
| Injector temperature: | 250° C. |
| Detector temperature: | 250° C. (FID) |
| Split: | 1 : 50 |
| Injection volume: | 1 µL |

Substances

Compound 1 (1R)-(1S,2S,3R,5S)-pinanediol-1-ammoniumtrifluoroacetate-3-methylbutane-1-boronate

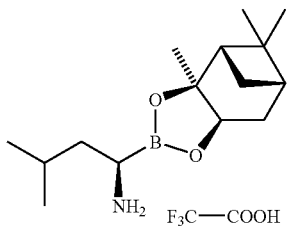

Compound 2 (1S)-(1S,2S,3R,5S)-pinanediol-1-ammoniumtrifluoroacetate-3-methylbutane-1-boronate

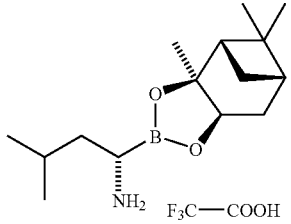

Stability of the Solution

A stock solution of compound 1 was prepared by weighing 150.13 mg of compound 1 into a 10-mL volumetric flask and bringing it to volume with Solvent A. Stability of this solution was tested at ambient temperature over 48 hours. The stock solution was filled in 6 separate GC vials. Injections onto the GC system were carried out from these vials after 0, 12, 24, 48, and 72 hours (double injection out of each vial. The area % of compound 1 and compound 2 were determined. No changes in area % were observed, indicating that the solution is stable over 72 hours at ambient temperature.

Specificity

Approximately 150 mg of a sample comprising compound 1 and compound 2 were dissolved in Solvent A and injected to the GC chromatographic system. The peak for compound 1 was well separated from the peak for compound 2. Peak purity check by GC-MS showed no other components co-eluting with compound 1 or compound 2.

Limit of Detection

The limit of detection (LOD) was defined to be that concentration where the signal of compound 1 showed a signal to noise ratio of at least 3:1. A previous blank measurement was carried out to show that no other peaks interfered. The signal to noise ratio was calculated by the equation:

$$S/N = \frac{H(\text{signal})}{H(\text{baseline})}$$

S/N=signal to noise ratio
H(signal)=height of signal for compound 1 [mm]
H(baseline)=height of signal baseline [mm]

A sample concentration of 0.05% of the standard test sample concentration was injected and showed a signal to noise ratio of 4.3. Therefore, the limit of detection is 0.0075 mg/mL.

Limit of Quantitation

The limit of quantitation (LOQ) was defined to be that concentration where the signal of compound 1 showed a signal to noise ratio of at least 10:1. Signal to noise ratio was calculated as described above. A sample concentration of 0.1% of the standard sample concentration was injected and showed a signal to noise ratio of 10.1. Therefore, the limit of quantitation is 0.015 mg/mL.

Example 5

Purity Assay for
N-(2-Pyrazinecarbonyl)-L-phenylalanine-L-leucine boronic anhydride The purity of N-(2-pyrazinecarbonyl)-L-phenylalanine-L-leucine boronic anhydride (compound 3) was assayed by reverse phase HPLC.

Reagents: Water, HPLC grade
Acetonitrile, HPLC grade
Formic acid, ACS grade, 98% pure
3% Hydrogen peroxide, ACS grade or equivalent Instrument
High performance liquid chromatograph Autosampler capable of delivering 20-pt injections and maintaining a temperature of 5° C.
Pump capable of gradient delivery at 1.0 mL/min
UV detector capable of monitoring effluent at 270 nm
Column Symmetry C18 chromatographic column, 250 mm×4.6 mm ID, 5 μm, Waters, cat #WAT054275.

Sample Preparation: Approximately 50 mg of compound 3 were accurately weighed into a 50-mL volumetric flask. Mobile Phase B (5 mL) was added and the mixture was sonicated to dissolve compound 3 (approximately 30-60 seconds). The solution was allowed to reach room temperature, diluted to volume with Mobile Phase A, and mixed well. Each sample was prepared in duplicate and was stable for 7 days when stored at 2-8° C. protected from light.

HPLC Parameters:
Mobile phase A: acetonitrile/water/formic acid, 30:70:0.1 (v/v/v), degassed
Mobile phase B: acetonitrile/water/formic acid, 8020:0.1 (v/v/v), degassed Flow rate: 1.0 mL/min
Detector: UV at 270 nm
Injection Volume: 20 μL
Column Temp: ambient
Sample Tray Tamp: 5° C.
Gradient Program:

| Time | % A | % B |
|---|---|---|
| 0 | 100 | 0 |
| 15 | 100 | 0 |
| 30 | 0 | 100 |
| 45 | 0 | 100 |
| 47 | 100 | 0 |
| 55 | 100 | 0 |

Substances

Compound 3
N-(2-Pyrazinecarbonyl)-L-phenylalanine-L-leucine boronic anhydride

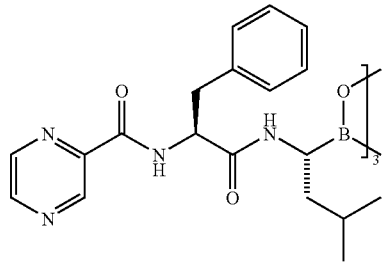

Compound 4
N-(2-Pyrazinecarbonyl)-D-phenylalanine-L-leucine boronic anhydride

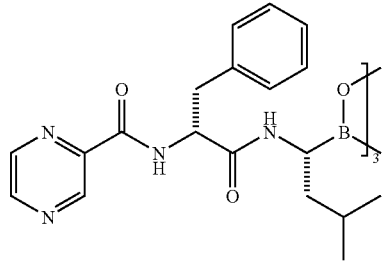

Compound 5
N-(2-Pyrazinecarbonyl)-L-phenylalanine-D-leucine boronic anhydride

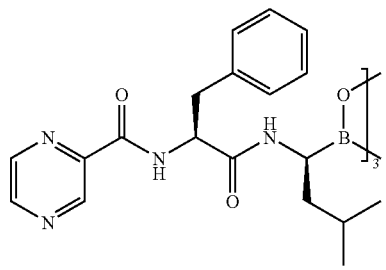

The retention time of compound 3 was typically between 10 and 14 minutes when using an HPLC system with a 1.3 minute dwell volume. Compounds 4 and 5 co-eluted at longer retention time, with a resolution of ≧2.0.

The relative retention of compound 3 in a sample chromatogram to that in the standard chromatogram was calculated according to the following equation:

$$R_r = \frac{t_{sam}}{t_{std}}$$

Where:
$R_r$=relative retention
$t_{sam}$=retention time of compound 3 peak in the sample chromatogram, minutes
$t_{std}$=retention time of the drug substance peak in the closest preceding standard chromatogram, minutes Assay results were calculated for each sample according to the following equation:

$$\% \text{ assay} = \frac{A_{sam}}{A_{std}} \times \frac{W_{std} \times P}{W_{sam}} \times \frac{1}{\left(\frac{100-M}{100}\right)} \times 100$$

Where:
$A_{sam}$=peak area response of compound 3 in the sample preparation
$A_{std}$=mean peak area response of compound 3 in the working standard preparation
$W_{std}$=weight of the standard, mg
P=assigned purity of the standard (decimal format)
$W_{sam}$=weight of the sample, mg
M=moisture content of the sample, %
100=conversion to percent Relative retention and impurity levels in each sample were calculated according to the following equations:

$$R_r = \frac{t_i}{t_{ds}}$$

Where:
$R_r$=relative retention
$t_i$=retention time of the individual impurity
$t_{ds}$=retention time of the compound 3 peak $$\% I_i = \frac{A_i \times W_{std} \times P \times DF \times RF_i}{A_{std,1\%} \times W_{sam}} \times 100$$

Where:
$I_i$=individual impurity
$A_i$=peak area response of individual impurity in the sample preparation
$A_{std,1\%}$=average peak area response of compound 3 in the 1% standard preparation
$W_{std}$=weight of the standard, mg
$W_{sam}$=weight of sample, mg
P=assigned purity of the standard (decimal format)
DF=dilution factor, 1/100
$RF_i$=relative response factor of individual impurity
100=conversion to percentage factor When assayed by this method, N-(2-pyrazinecarbonyl)-L-phenylalanine-L-leucineboronic anhydride from Example 2 showed total impurities of less than 1%.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention and appended claims.

What is claimed is:

1. A large-scale process for preparing a boronic ester compound of formula (I):

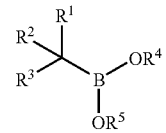

(I)

wherein:
$R^1$ is an optionally substituted aliphatic or aromatic group;
$R^2$ is hydrogen, a nucleofugic group, or an optionally substituted aliphatic or aromatic group;
$R^3$ is a nucleofugic group or an optionally substituted aliphatic or aromatic group;
$R^4$ and $R^5$ are together an optionally substituted aliphatic group, and $R^4$ and $R^5$, taken together with the intervening oxygen and boron atoms, form an optionally substituted 5- to 10-membered ring having 0 additional ring heteroatoms; and
none of the variables $R^1$-$R^5$ is substituted with a heteroaromatic group;

said process comprising:
(a) providing a boron "ate" complex of formula (II):

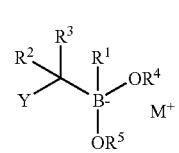

(II)

where
Y is a nucleofugic group;
$M^+$ is a cation; and
each of $R^1$ to $R^5$ is as defined above; and
(b) contacting the boron "ate" complex of formula (II) with a Lewis acid under conditions that afford the boronic ester compound of formula (I) said contacting step being conducted in a reaction mixture comprising:
(i) a coordinating ether solvent that has low miscibility with water; or
(ii) an ether solvent that has low miscibility with water and a coordinating co-solvent, provided that the coordinating co-solvent constitutes no more than about 20% v/v of the reaction mixture;
wherein the solubility of water in the ether solvent in (i) or (ii) that has low miscibility with water is less than about 5% w/w; and
wherein the ether solvent in (i) or (ii) that has low miscibility with water constitutes at least about 70% v/v of the reaction mixture.

2. The process of claim 1, wherein the reaction mixture comprises a coordinating co-solvent.

3. The process of claim 2, wherein the coordinating co-solvent is selected from the group consisting of tetrahydrofuran, dioxane, water, and mixtures thereof.

4. The process of claim 3, wherein the coordinating co-solvent constitutes no more than about 15% v/v of the reaction mixture.

5. The process of claim 1, wherein the solubility of water in the ether solvent that has low miscibility with water is less than about 2% w/w.

6. The process of claim 5, wherein the ether solvent that has low miscibility with water is selected from the group consisting of tert-butyl methyl ether, tert-butyl ethyl ether, tert-amyl methyl ether, isopropyl ether, and mixtures thereof.

7. The process of claim 1, wherein at least about 5 moles of the boron "ate" complex of formula (II) are provided in step (a).

8. The process of claim 1, wherein at least about 20 moles of the boron "ate" complex of formula (II) are provided in step (a).

9. The process of claim 1, wherein at least about 50 moles of the boron "ate" complex of formula (II) are provided in step (a).

10. The process of claim 1, wherein at least about 100 moles of the boron "ate" complex of formula (II) are provided in step (a).

11. The process of claim 1, wherein the Lewis acid is selected from the group consisting of zinc chloride, zinc bromide, ferric chloride, and ferric bromide.

12. The process of claim 11, wherein the Lewis acid is moist.

13. The process of claim 12, wherein in step (a) the boron "ate" complex of formula (II) is provided in a solution comprising an ether solvent that has low miscibility with water, and the contacting step (b) comprises the steps:
   (i) providing a solution comprising a Lewis acid and tetrahydrofuran; and
   (ii) adding the Lewis acid solution to the solution of the boron "ate" complex of formula (II) from step (a).

14. The process of claim 11, wherein in step (a) the boron "ate" complex of formula (II) is provided in a solution comprising an ether solvent that has low miscibility with water, and the contacting step (b) comprises the steps:
   (i) providing a solution comprising a Lewis acid and water; and
   (ii) adding the Lewis acid solution to the solution of the boron "ate" complex of formula (II) from step (a).

15. The process of claim 1, wherein Y is a halogen.

16. The process of claim 1, wherein Y is chloro.

17. The process of claim 1, wherein $R^1$ is $C_{1-8}$ aliphatic, $C_{6-10}$ aryl, or $(C_{6-10}$ aryl)$(C_{1-6}$ aliphatic).

18. The process of claim 1, wherein $M^+$ is selected from the group consisting of $Li^+$, $Na^+$, and $K^+$.

19. The process of claim 1, wherein $R^4$ and $R^5$ together are a chiral moiety.

20. The process of claim 19, wherein the boron "ate" complex of formula (II) is:

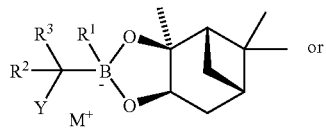 or

-continued

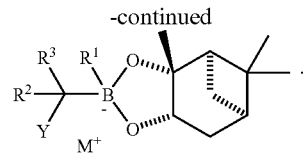

21. The process of claim 19, wherein step (b) provides the boronic ester compound of formula (I) wherein the carbon atom bearing $R^1$, $R^2$, and $R^3$ is a chiral center having a diastereomeric ratio of at least about 96:4 relative to a chiral center in the $R^4$—$R^5$ chiral moiety.

22. The process of claim 19, wherein step (b) provides the boronic ester compound of formula (I) wherein the carbon atom bearing $R^1$, $R^2$, and $R^3$ is a chiral center having a diastereomeric ratio of at least about 97:3 relative to a chiral center in the $R^4$—$R^5$ chiral moiety.

23. The process of claim 19, characterized by at least one of the following features:
   (a) the contacting step (b) is conducted in a reaction mixture comprising tert-butyl methyl ether;
   (b) the Lewis acid is zinc chloride;
   (c) at least about 5 moles of the boronic ester of formula (II) are provided in step (a);
   (d) the contacting step (b) is performed at a reaction temperature in the range of about −60° C. to about −30° C.;
   (e) the Lewis acid is moist;
   (f) Y is chloro;
   (g) $R^3$ is chloro;
   (h) $R^2$ is hydrogen; and
   (i) $R^1$ is $C_{1-4}$ aliphatic.

24. The process of claim 23, characterized by at least two of the features (a)-(i).

25. The process of claim 23, characterized by at least three of the features (a)-(i).

26. The process of claim 23, characterized by all nine of the features (a)-(i).

27. The process of claim 21, further comprising:
   (c) washing the reaction mixture with an aqueous solution; and
   (d) concentrating the washed reaction mixture by removal of solvents to afford a residue comprising the boronic ester compound of formula (I).

28. The process of claim 27, wherein the residue comprises at least about five moles of the boronic ester compound of formula (I).

29. The process of claim 28, wherein the boronic ester compound of formula (I) present in the residue has a diastereomeric ratio of at least about 96:4 at the carbon atom bearing $R^1$, $R^2$, and $R^3$, relative to a chiral center in the $R^4$—$R^5$ chiral moiety.

30. The process of claim 28, wherein the boronic ester compound of formula (I) present in the residue has a diastereomeric ratio of at least about 97:3 at the carbon atom bearing $R^1$, $R^2$, and $R^3$, relative to a chiral center in the $R^4$—$R^5$ chiral moiety.

* * * * *